(12) United States Patent
Galbraith et al.

(10) Patent No.: US 10,507,300 B2
(45) Date of Patent: Dec. 17, 2019

(54) ULTRA RAPID CYCLE PORTABLE OXYGEN CONCENTRATOR

(71) Applicant: SEPARATION DESIGN GROUP IP HOLDINGS, LLC, Waynesburg, PA (US)

(72) Inventors: Stephen Douglas Galbraith, Holbrook, PA (US); Robert B. Lacount, Waynesburg, PA (US)

(73) Assignee: SEPARATION DESIGN GROUP IP HOLDINGS, LLC, Waynesburg, PA (US)

( * ) Notice: Subject to any disclaimer, the term of this patent is extended or adjusted under 35 U.S.C. 154(b) by 72 days.

(21) Appl. No.: 15/715,600

(22) Filed: Sep. 26, 2017

(65) Prior Publication Data

US 2018/0050167 A1    Feb. 22, 2018

Related U.S. Application Data

(63) Continuation of application No. 14/876,133, filed on Oct. 6, 2015, now Pat. No. 9,839,757, which is a
(Continued)

(51) Int. Cl.
*B01D 53/26* (2006.01)
*A61M 16/10* (2006.01)
(Continued)

(52) U.S. Cl.
CPC ...... *A61M 16/101* (2014.02); *A61M 16/0003* (2014.02); *A61M 16/0063* (2014.02);
(Continued)

(58) Field of Classification Search
CPC .......... A61M 16/0003; A61M 16/0063; A61M 16/0066; A61M 16/0672; A61M 16/0875;
(Continued)

(56) References Cited

U.S. PATENT DOCUMENTS

| | | | |
|---|---|---|---|
| 3,952,239 A | | 4/1976 | Owings et al. |
| 4,342,573 A | * | 8/1982 | McCombs ......... B01D 53/0446 55/494 |

(Continued)

FOREIGN PATENT DOCUMENTS

| | | |
|---|---|---|
| EP | 2485794 A2 | 8/2012 |
| FR | 2851935 A1 | 9/2004 |

(Continued)

OTHER PUBLICATIONS

Machine-generated English translation of JP 2007-044116 A, published Feb. 2007.*

(Continued)

*Primary Examiner* — Frank M Lawrence, Jr.
(74) *Attorney, Agent, or Firm* — Panitch Schwarze Belisario & Nadel LLP

(57) ABSTRACT

Lightweight, portable oxygen concentrators that operate using an ultra rapid, sub one second, adsorption cycle based on advanced molecular sieve materials are disclosed. The amount of sieve material utilized is a fraction of that used in conventional portable devices. This dramatically reduces the volume, weight, and cost of the device. Innovations in valve configuration, moisture control, case and battery design, and replaceable sieve module are described. Patients with breathing disorders and others requiring medical oxygen are provided with a long lasting, low cost alternative to existing portable oxygen supply devices.

9 Claims, 16 Drawing Sheets

Related U.S. Application Data continuation of application No. 14/519,868, filed on Oct. 21, 2014, now Pat. No. 9,199,055, which is a continuation of application No. 13/499,943, filed as application No. PCT/US2010/051419 on Oct. 5, 2010, now Pat. No. 8,894,751.

(60) Provisional application No. 61/264,069, filed on Nov. 24, 2009, provisional application No. 61/248,712, filed on Oct. 5, 2009.

(51) Int. Cl.
    *B01D 53/02*    (2006.01)
    *B01D 53/04*    (2006.01)
    *B01D 53/047*   (2006.01)
    *A61M 16/06*    (2006.01)
    *A61M 16/00*    (2006.01)
    *A61M 16/20*    (2006.01)
    *A61M 16/08*    (2006.01)

(52) U.S. Cl.
    CPC .... *A61M 16/0666* (2013.01); *A61M 16/0672* (2014.02); *A61M 16/0875* (2013.01); *A61M 16/105* (2013.01); *A61M 16/1005* (2014.02); *A61M 16/20* (2013.01); *B01D 53/02* (2013.01); *B01D 53/0415* (2013.01); *B01D 53/0473* (2013.01); *B01D 53/26* (2013.01); *A61M 16/107* (2014.02); *A61M 2016/1025* (2013.01); *A61M 2202/0208* (2013.01); *A61M 2205/02* (2013.01); *A61M 2205/3327* (2013.01); *A61M 2205/3334* (2013.01); *A61M 2205/42* (2013.01); *A61M 2205/75* (2013.01); *A61M 2205/8206* (2013.01); *B01D 2253/108* (2013.01); *B01D 2253/304* (2013.01); *B01D 2256/12* (2013.01); *B01D 2257/102* (2013.01); *B01D 2259/4533* (2013.01); *B01D 2259/4541* (2013.01); *Y10T 137/85938* (2015.04)

(58) Field of Classification Search
    CPC ............ A61M 16/1005; A61M 16/101; A61M 16/105; A61M 16/107; A61M 16/20; A61M 2016/1025; A61M 2202/0208; A61M 2205/02; A61M 2205/3327; A61M 2205/3334; A61M 2205/42; A61M 2205/75; A61M 2205/8206; B01D 53/02; B01D 53/0415; B01D 53/0473; B01D 53/26; B01D 2253/108; B01D 2253/304; B01D 2256/12; B01D 2257/102; B01D 2259/4533; B01D 2259/4541; Y10T 137/85938
    USPC ................................ 96/121, 131; 95/52, 117
    See application file for complete search history.

(56) References Cited

U.S. PATENT DOCUMENTS

| | | | |
|---|---|---|---|
| 4,373,938 A | 2/1983 | McCombs | |
| 4,378,982 A | 4/1983 | McCombs | |
| 4,509,959 A | 4/1985 | McCombs | |
| 4,584,001 A | 4/1986 | Dechene | |
| 4,822,384 A * | 4/1989 | Kato | B01D 53/0407 55/417 |
| 5,288,306 A | 2/1994 | Aibe et al. | |
| 6,515,451 B2 | 2/2003 | Watson et al. | |
| 6,592,731 B1 | 7/2003 | Lawless | |
| 6,916,360 B2 | 7/2005 | Seguin et al. | |
| 7,204,249 B1 | 4/2007 | Richey, II et al. | |
| 7,273,051 B2 | 9/2007 | Whitley et al. | |
| 7,294,170 B2 | 11/2007 | Richey, II et al. | |
| 7,510,601 B2 | 3/2009 | Whitley et al. | |
| 7,625,437 B2 | 12/2009 | Heer | |
| 7,763,103 B2 | 7/2010 | Dolensky et al. | |
| 7,828,878 B2 | 11/2010 | Zhong et al. | |
| 8,192,526 B2 | 6/2012 | Zhong et al. | |
| 8,377,181 B2 | 2/2013 | Taylor et al. | |
| 8,388,745 B1 | 3/2013 | Pelletier et al. | |
| 8,894,751 B2 | 11/2014 | Galbraith et al. | |
| 9,199,055 B2 | 12/2015 | Galbraith et al. | |
| 2002/0096174 A1 | 7/2002 | Hill et al. | |
| 2003/0010205 A1* | 1/2003 | Bikson | B01D 46/003 95/52 |
| 2004/0000233 A1* | 1/2004 | Nichols | B01D 53/22 95/52 |
| 2004/0107831 A1 | 6/2004 | Graham et al. | |
| 2005/0022815 A1 | 2/2005 | Frola | |
| 2005/0103341 A1* | 5/2005 | Deane | B01D 53/053 128/204.26 |
| 2006/0117957 A1 | 6/2006 | McCombs et al. | |
| 2006/0137522 A1 | 6/2006 | Nishimura et al. | |
| 2006/0174874 A1 | 8/2006 | Jagger et al. | |
| 2006/0174881 A1 | 8/2006 | Jagger et al. | |
| 2006/0244417 A1 | 11/2006 | Tsai et al. | |
| 2007/0227360 A1 | 10/2007 | Atlas et al. | |
| 2008/0022851 A1* | 1/2008 | Lee | B01D 53/047 95/96 |
| 2008/0034975 A1 | 2/2008 | Chambers et al. | |
| 2009/0071333 A1* | 3/2009 | LaBuda | B01D 53/02 95/96 |
| 2009/0145428 A1 | 6/2009 | Sward et al. | |
| 2009/0205493 A1* | 8/2009 | Thompson | B01D 53/0476 95/130 |
| 2010/0052293 A1 | 3/2010 | Brooks et al. | |
| 2012/0266883 A1 | 10/2012 | Taylor et al. | |
| 2016/0022951 A1 | 1/2016 | Galbraith | |

FOREIGN PATENT DOCUMENTS

| | | | |
|---|---|---|---|
| FR | 2916654 A1 | | 12/2008 |
| GB | 2013101 A | | 8/1979 |
| JP | 05-049697 A | * | 3/1993 |
| JP | 2007-044115 A | * | 2/2007 |
| WO | WO-2011/044091 A2 | | 4/2011 |

OTHER PUBLICATIONS

Joint Request to File Settlement Agreement as Business Confidential filed on Nov. 6, 2017 for Inter Partes Review filed by Separation Design Group IP Holdings, LLC, on Aug. 21, 2017, for U.S. Pat. No. 8,894,751, which was filed at the Patent Trial and Appeal Board on Nov. 18, 2016; Case No. IPR2017-00300 (3 pages).
Joint Request to Terminate Inter Partes Review Proceeding filed on Nov. 6, 2017 for Inter Partes Review filed by Separation Design Group IP Holdings, LLC, on Aug. 21, 2017, for U.S. Pat. No. 8,894,751, which was filed at the Patent Trial and Appeal Board on Nov. 18, 2016; Case No. IPR2017-00300 (5 pages).
Order of Termination of the Proceedings 35 U.S.C. sec 317(a) and 37 C.F.R. sec 42.72 issued on Nov. 7, 2017 for Inter Partes Review filed by Separation Design Group IP Holdings, LLC, on Aug. 21, 2017, for U.S. Pat. No. 8,894,751, which was filed at the Patent Trial and Appeal Board on Nov. 18, 2016; Case No. IPR2017-00300 (3 pages).
Joint Request to File Settlement Agreement as Business Confidential filed on Nov. 6, 2017 for Inter Partes Review of U.S. Pat. No. 9,199,055, filed at the Patent Trial and Appeal Board on Dec. 8, 2016, Case No. IPR2017-00453 (3 pages).
Joint Motion to Terminate filed on Nov. 6, 2017 for Inter Partes Review of U.S. Pat. No. 9,199,055, filed at the Patent Trial and Appeal Board on Dec. 8, 2016, Case No. IPR2017-00453 (5 pages).
Order of Termination of the Proceedings 35 U.S.C. sec 317(a) and 37 C.F.R. sec 42.72 issued on Nov. 7, 2017 for Inter Partes Review of U.S. Pat. No. 9,199,055, filed at the Patent Trial and Appeal Board on Dec. 8, 2016, Case No. IPR2017-00453 (3 pages).
Notice of Allowance dated Oct. 235, 2017 by the U.S. Patent and Trademark Office for U.S. Appl. No. 14/876,133, filed Oct. 6, 2015

(56) References Cited

OTHER PUBLICATIONS and published as US 2016/0022951 on Jan. 28, 2016 (Inventor—Galbraith et al.; Applicant—Separation Design Group IP Holdings, LLC; (9 pages).
Supplemental European Search Report dated Nov. 20, 2013 by the European Patent Office for Application No. 10822515.2, which was published as EP 2485794 on Sep. 3, 2012 (Inventor—Galbraith // Applicant—Separation Design Group, LLC) (6 pages).
International Search Report and Written Opinion dated Jun. 21, 2011 for PCT Application No. PCT/US2010/051419, which was published as WO 2011/044091 on Apr. 14, 2012 (Inventor—Galbraith // Applicant—Separation Design Group, LLC) (6 pages).
International Preliminary Report on Patentability dated Apr. 11, 2012 for PCT Application No. PCT/US2010/051419, which was published as WO 2011/044091 on Apr. 14, 2012 (Inventor—Galbraith // Applicant—Separation Design Group, LLC) (6 pages).
Amendment after Notice of Allowance submitted on Oct. 22, 2014 to the USPTO for U.S. Appl. No. 13/499,943, which was published as US 2012-0192864 on Aug. 2, 2012 (Inventor—Galbraith // Applicant—Separation Design Group, LLC) (6 pages).
Notice of Allowance dated Sep. 22, 2014 by the USPTO for U.S. Appl. No. 13/499,943, which was published as US 2012-0192864 on Aug. 2, 2012 (Inventor—Galbraith Applicant—Separation Design Group, LLC.; (10 pages).
Amended Response to Restriction Requirement submitted on Aug. 27, 2014 to the USPTO for U.S. Appl. No. 13/499,943, which was published as US 2012-0192864 on Aug. 2, 2012 (Inventor—Galbraith Applicant—Separation Design Group, LLC.; (9 pages).
Response to Restriction Requirement submitted on Aug. 22, 2014 to the USPTO for U.S. Appl. No. 13/499,943, which was published as US 2012-0192864 on Aug. 2, 2012 (Inventor—Galbraith // Applicant—Separation Design Group, LLC) (10 pages).
Restriction Requirement dated Jun. 24, 2014 by the USPTO for U.S. Appl. No. 13/499,943, which was published as US 2012-0192864 on Aug. 2, 2012 (Inventor—Galbraith // Applicant—Separation Design Group, LLC) (7 pages).
Non-Final Office Action dated May 15, 2015 by the USPTO for U.S. Appl. No. 14/519,868, filed Oct. 21, 2014 and published as US-2015-0101603 on Apr. 16, 2015 (Inventor—Galbraith // Applicant—Separation Design Group, LLC) (8 pages).
Response to Non-Final Office Action filed on Aug. 14, 2015 for U.S. Appl. No. 14/519,868, filed on Oct. 21, 2014 and published as US-2015-0101603 on Apr. 16, 2015 (Inventor—Galbraith // Applicant—Separation Design Group, LLC) (9 pages).
Notice of Allowance dated Aug. 28, 2015 by the USPTO for U.S. Appl. No. 14/519,868, filed Oct. 21, 2014 and published as US-2015-0101603 on Apr. 16, 2015 (Inventor—Galbraith // Applicant—Separation Design Group, LLC) (7 pages).
Amendment after Notice of Allowance filed on Sep. 28, 2015 for U.S. Appl. No. 14/519,868, filed on Oct. 21, 2014 and published as US-2015-0101603 on Apr. 16, 2015 (Inventor—Galbraith // Applicant—Separation Design Group, LLC) (6 pages).
Complaint filed on Oct. 23, 2015 by Separation Design Group IP Holdings, LLC, in the U.S. District Court for the Central District of California (*Separation Design Group IP Holdings, LLC v. Inogen, Inc.* // Case No. 2:15-cv-08323) (80 pages).
First Amended Complaint filed on Dec. 7, 2015 by Separation Design Group IP Holdings, LLC, in the U.S. District Court for the Central District of California (*Separation Design Group IP Holdings, LLC v. Inogen, Inc.* // Case No. 2:15-cv-08323) (114 pages).
Answer to First Amended Complaint filed on Jan. 22, 2016 by Inogen, Inc., in the U.S. District Court for the Central District of California (*Separation Design Group IP Holdings, LLC v. Inogen, Inc.* // Case No. 2:15-cv-08323) (12 pages).
First Amended Answer to First Amended Complaint filed on May 27, 2016 by Inogen, Inc., in the U.S. District Court for the Central District of California (*Separation Design Group IP Holdings, LLC v. Inogen, Inc.* // Case No. 2:15-cv-08323) (188 pages).

Counterclaims filed on May 27, 2016 by Inogen, Inc., in the U.S. District Court for the Central District of California (*Separation Design Group IP Holdings, LLC v. Inogen, Inc.* // Case No. 2:15-cv-08323) (158 pages).
Opening Claim Construction Brief filed on Jun. 3, 2016 by Inogen, Inc., in the U.S. Distrcit Court for the Central District of California (*Separation Design Group IP Holdings, LLC v. Inogen, Inc.* // Case No. 2:15-cv-08323) (36 pages).
Opening Claim Construction Brief filed on Jun. 3, 2016 by Separation Design Group IP Holdings, LLC, in the U.S. Distrcit Court for the Central District of California (*Separation Design Group IP Holdings, LLC v. Inogen, Inc.* // Case No. 2:15-cv-08323) (32 pages).
Plaintiffs Notice of Motion and Motion for Leave to file a Second Amended Complaint, filed on Jul. 22, 2016 by Separation Design Group IP Holdings, LLC, in the U.S. District Court for the Central District of California (*Separation Design Group IP Holdings, LLC v. Inogen, Inc.* // Case No. 2:15-cv-08323) (58 pages).
Inogen's Notice of Supplemental Authority Regarding Claim Construction filed on Aug. 2, 2016 by Inogen, Inc., in the U.S. District Court for the Central District of California (*Separation Design Group IP Holdings, LLC v. Inogen, Inc.* // Case No. 2:15-cv-08323) (18 pages).
Joint Stipulation to Amend Expert Reporting Deadlines, filed on Sep. 8, 2016 by Separation Design Group IP Holdings, LLC, and Inogen, Inc., in the U.S. District Court for the Central District of California (*Separation Design Group IP Holdings, LLC v. Inogen, Inc.* // Case No. 2:15-cv-08323) (2 pages).
Order Granting Joint Stipulation to Amend Expert Reporting Deadlines, issued on Sep. 15, 2016 by Separation Design Group IP Holdings, LLC, and Inogen, Inc., in the U.S. District Court for the Central District of California (*Separation Design Group IP Holdings, LLC v. Inogen, Inc.* // Case No. 2:15-cv-08323) (2 pages).
Minutes of Hearing on Plaintiff's Motion for Leave to file a Second Amended Complaint, issued on Oct. 3, 2016 by Separation Design Group IP Holdings, LLC, in the U.S. District Court for the Central District of California (*Separation Design Group IP Holdings, LLC v. Inogen, Inc.* // Case No. 2:15-cv-08323) (1 page).
Order Regarding Claim Construction, issued on Oct. 21, 2016 by the U.S. District Court for the Central District of California (*Separation Design Group IP Holdings, LLC v. Inogen, Inc.* // Case No. 2:15-cv-08323) (29 pages).
Order Granting Plaintiff's Motion for Leave to File a Second Amended Complaint, issued on Oct. 21, 2016 the U.S. District Court for the Central District of California (*Separation Design Group IP Holdings, LLC v. Inogen, Inc.* // Case No. 2:15-cv-08323) (4 pages).
Joint Report Regarding Case Schedule filed by Separation Design Group IP Holdings, LLC, and Inogen, Inc., in the U.S. District Court for the Central District of California (*Separation Design Group IP Holdings, LLC v. Inogen, Inc.* // Case No. 2:15-cv-08323) (8 pages).
Notice of Lodging Proposed Order re Joint Report Regarding Case Schedule filed by Separation Design Group IP Holdings, LLC, and Inogen, Inc., in the U.S. District Court for the Central District of California (*Separation Design Group IP Holdings, LLC v. Inogen, Inc.* // Case No. 2:15-cv- 08323) (7 pages).
Petition by Inogen, Inc., for Inter Partes Review of U.S. Pat. No. 8,894,751, filed at the Patent Trial and Appeal Board on Nov. 18, 2016, Case No. IPR2017-00300 (95 pages).
Exhibit 1001—U.S. Pat. No. 8,894,751, filed at the Patent Trial and Appeal Board on Nov. 18, 2016, Case No. IPR2017-00300 (32 pages).
Exhibit 1002—U.S. Patent Application Publication No. 2006/0117957, filed at the Patent Trial and Appeal Board on Nov. 18, 2016, Case No. IPR2017-00300 (17 pages).
Exhibit 1003—U.S. Patent Application Publication No. 2007/0137487, filed at the Patent Trial and Appeal Board on Nov. 18, 2016, Case No. IPR2017-00300 (17 pages).
Exhibit 1004—U.S. Pat. No. 7,279,029, filed at the Patent Trial and Appeal Board on Nov. 18, 2016, Case No. IPR2017-00300 (27 pages).

(56) References Cited

OTHER PUBLICATIONS

Exhibit 1005—U.S. Patent Application Publication No. 2006/0174874, filed at the Patent Trial and Appeal Board on Nov. 18, 2016, Case No. IPR2017-00300 (35 pages).
Exhibit 1006—U.S. Patent Application Publication No. 2006/0230931, filed at the Patent Trial and Appeal Board on Nov. 18, 2016, Case No. IPR2017-00300 (30 pages).
Exhibit 1007—U.S. Pat. No. 8,016,925, filed at the Patent Trial and Appeal Board on Nov. 18, 2016, Case No. IPR2017-00300 (20 pages).
Exhibit 1008—U.S. Pat. No. 6,764,534, filed at the Patent Trial and Appeal Board on Nov. 18, 2016, Case No. IPR2017-00300 (42 pages).
Exhibit 1009—Excerpts from the file history of U.S. Pat. No. 8,894,751, filed at the Patent Trial and Appeal Board on Nov. 18, 2016, Case No. IPR2017-00300 (99 pages).
Exhibit 1010—U.S. Pat. No. 9,199,055, filed at the Patent Trial and Appeal Board on Nov. 18, 2016, Case No. IPR2017-00300 (31 pages).
Exhibit 1011—Declaration of Brenton Taylor in Support of the Petition for Inter Partes Review of U.S. Pat. No. 8,894,751, filed at the Patent Trial and Appeal Board on Nov. 18, 2016, Case No. IPR2017-00300 (133 pages).
Exhibit 1012—Complaint for Patent Infringement, filed at the Patent Trial and Appeal Board on Nov. 18, 2016, Case No. IPR2017-00300 (16 pages).
Exhibit 1013—Proof of Service of Summons and Complaint, filed at the Patent Trial and Appeal Board on Nov. 18, 2016, Case No. IPR2017-00300 (2 pages).
Exhibit 1014—Claim Construction Order, filed at the Patent Trial and Appeal Board on Nov. 18, 2016, Case No. IPR2017-00300 (29 pages).
Exhibit 1015—Declaration of Peter Bliss, filed at the Patent Trial and Appeal Board on Nov. 18, 2016, Case No. IPR2017-00300 (10 pages).
Exhibit 1016—Separation Design Group IP Holdings, LLC's Opening Claim Construction Brief, filed at the Patent Trial and Appeal Board on Nov. 18, 2016, Case No. IPR2017-00300 (32 pages).
Exhibit 1017—Separation Design Group IP Holdings, LLC's Responsive Claim Construction Brief, filed at the Patent Trial and Appeal Board on Nov. 18, 2016, Case No. IPR2017-00300 (12 pages).
Exhibit 1020—U.S. Pat. No. 3,386,802, filed at the Patent Trial and Appeal Board on Nov. 18, 2016, Case No. IPR2017-00300 (6 pages).
Exhibit 1021—U.S. Pat. No. 4,094,775, filed at the Patent Trial and Appeal Board on Nov. 18, 2016, Case No. IPR2017-00300 (6 pages).
Exhibit 1022—U.S. Pat. No. 4,530,706, filed at the Patent Trial and Appeal Board on Nov. 18, 2016, Case No. IPR2017-00300 (5 pages).
Exhibit 1023—U.S. Pat. No. 4,948,391, filed at the Patent Trial and Appeal Board on Nov. 18, 2016, Case No. IPR2017-00300 (18 pages).
Exhibit 1024—U.S. Pat. No. 5,001,289, filed at the Patent Trial and Appeal Board on Nov. 18, 2016, Case No. IPR2017-00300 (7 pages).
Exhibit 1025—U.S. Pat. No. 6,149,138, filed at the Patent Trial and Appeal Board on Nov. 18, 2016, Case No. IPR2017-00300 (7 pages).
Exhibit 1026—U.S. Pat. No. 6,551,384, filed at the Patent Trial and Appeal Board on Nov. 18, 2016, Case No. IPR2017-00300 (13 pages).
Exhibit 1027—U.S. Pat. No. 6,551,658, filed at the Patent Trial and Appeal Board on Nov. 18, 2016, Case No. IPR2017-00300 (17 pages).
Exhibit 1028—U.S. Pat. No. 6,755,895, filed at the Patent Trial and Appeal Board on Nov. 18, 2016, Case No. IPR2017-00300 (19 pages).
Exhibit 1029—U.S. Pat. No. 7,144,446, filed at the Patent Trial and Appeal Board on Nov. 18, 2016, Case No. IPR2017-00300 (4 pages).
Exhibit 1030—U.S. Pat. No. 7,828,878, filed at the Patent Trial and Appeal Board on Nov. 18, 2016, Case No. IPR2017-00300 (11 pages).
Exhibit 1031—U.S. Pat. No. 8,114,194, filed at the Patent Trial and Appeal Board on Nov. 18, 2016, Case No. IPR2017-00300 (6 pages).
Exhibit 1032—U.S. Pat. No. 8,388,745, filed at the Patent Trial and Appeal Board on Nov. 18, 2016, Case No. IPR2017-00300 (10 pages).
Exhibit 1033—U.S. Patent Application Publication No. 2004/0107831, filed at the Patent Trial and Appeal Board on Nov. 18, 2016, Case No. IPR2017-00300 (19 pages).
Exhibit 1034—U.S. Patent Application Publication No. 2005/0045041, filed at the Patent Trial and Appeal Board on Nov. 18, 2016, Case No. IPR2017-00300 (36 pages).
Exhibit 1035—U.S. Patent Application Publication No. 2005/0103341, filed at the Patent Trial and Appeal Board on Nov. 18, 2016, Case No. IPR2017-00300 (46 pages).
Exhibit 1036—U.S. Patent Application Publication No. 2006/0000223, filed at the Patent Trial and Appeal Board on Nov. 18, 2016, Case No. IPR2017-00300 (23 pages).
Exhibit 1037—U.S. Patent Application Publication No. 2006/0230931, filed at the Patent Trial and Appeal Board on Nov. 18, 2016, Case No. IPR2017-00300 (30 pages).
Exhibit 1038—U.S. Patent Application Publication No. 2009/0145428, filed at the Patent Trial and Appeal Board on Nov. 18, 2016, Case No. IPR2017-00300 (37 pages).
Exhibit 1039—U.S. Patent Application Publication No. 2010/0196213, filed at the Patent Trial and Appeal Board on Nov. 18, 2016, Case No. IPR2017-00300 (20 pages).
Exhibit 1040—European Patent Application Publication No. 0013680, filed at the Patent Trial and Appeal Board on Nov. 18, 2016, Case No. IPR2017-00300 (35 pages).
Order Granting Joint Report Regarding Case Schedule issued on Nov. 3, 2016, by the U.S. District Court for the Central District of California (*Separation Design Group IP Holdings, LLC v. Inogen, Inc.* // Case No. 2:15-cv-08323) (3 pages).
Second Amended Complaint filed on Nov. 4, 2016 by Separation Design Group IP Holdings, LLC, in the U.S. District Court for the Central District of California (*Separation Design Group IP Holdings, LLC v. Inogen, Inc.* // Case No. 2:15-cv-08323) (116 pages).
Answer to Second Amended Complaint filed on Nov. 21, 2016 by Inogen, Inc., in the U.S. District Court for the Central District of California (*Separation Design Group IP Holdings, LLC v. Inogen, Inc.* // Case No. 2:15-cv-08323) (167 pages).
Petition by Inogen, Inc., for Inter Partes Review of U.S. Pat. No. 9,199,055, filed at the Patent Trial and Appeal Board on Dec. 8, 2016, Case No. IPR2017-00453 (105 pages).
Exhibit 1001—U.S. Pat. No. 9,199,055, filed at the Patent Trial and Appeal Board on Nov. 18, 2016, Case No. IPR2017-00453 (31 pages).
Exhibit 1002—U.S. Patent Publication No. 2006/0117957 (McCombs), filed at the Patent Trial and Appeal Board on Nov. 18, 2016, Case No. IPR2017-00453 (17 pages).
Exhibit 1003—U.S. Patent Publication No. 2007/0137487 (Whitley), filed at the Patent Trial and Appeal Board on Nov. 18, 2016, Case No. IPR2017-00453 (27 pages).
Exhibit 1004—U.S. Pat. No. 7,279,029 (Occhialini), filed at the Patent Trial and Appeal Board on Nov. 18, 2016, Case No. IPR2017-00453 (27 pages).
Exhibit 1005—U.S. Patent Publication No. 2006/0174874 (Jagger), filed at the Patent Trial and Appeal Board on Nov. 18, 2016, Case No. IPR2017-00453 (35 pages).
Exhibit 1006—U.S. Patent Publication No. 2006/0230931 (Bliss), filed at the Patent Trial and Appeal Board on Nov. 18, 2016, Case No. IPR2017-00453 (30 pages).
Exhibit 1007—U.S. Pat. No. 8,016,925 (McCombs '925), filed at the Patent Trial and Appeal Board on Nov. 18, 2016, Case No. IPR2017-00453 (20 pages).

(56) References Cited

OTHER PUBLICATIONS

Exhibit 1008—U.S. Pat. No. 6,764,534 (McCombs '534), filed at the Patent Trial and Appeal Board on Nov. 18, 2016, Case No. IPR2017-00453 (42 pages).
Exhibit 1009—Excerpts from File Histories of U.S. Pat. Nos. 8,894,751 and 9,199,055, filed at the Patent Trial and Appeal Board on Nov. 18, 2016, Case No. IPR2017-00453 (236 pages).
Exhibit 1010—U.S. Pat. No. 8,894,751, filed at the Patent Trial and Appeal Board on Nov. 18, 2016, Case No. IPR2017-00453 (32 pages).
Exhibit 1011—Declaration of Brenton A. Taylor, filed at the Patent Trial and Appeal Board on Nov. 18, 2016, Case No. IPR2017-00453 (159 pages).
Exhibit 1012—First Amended Complaint of Separation Design Group IP Holdings, LLC, *Separation Design Group IP Holdings, LLC* v. *Inogen, Inc.*, Case No. 2:15-cv-08323-JAK-JPR (C.D. Cal.), filed at the Patent Trial and Appeal Board on Nov. 18, 2016, Case No. IPR2017-00453 (18 pages).
Exhibit 1013—Joint Stipulation to Extend Time to Respond to Plaintiff's First Amended Complaint, *Separation Design Group IP Holdings, LLC* v. *Inogen, Inc.*, Case No. 2:15-cv-08323-JAK-JPR (C.D. Cal.), filed at the Patent Trial and Appeal Board on Nov. 18, 2016, Case No. IPR2017-00453 (2 pages).
Exhibit 1014—Claim Construction Order dated Oct. 21, 2016 in *Separation Design Group IP Holdings, LLC* v. *Inogen, Inc.*, Case No. 2:15-cv-08323-JAK-JPR (C.D. Cal.), filed at the Patent Trial and Appeal Board on Nov. 18, 2016, Case No. IPR2017-00453 (29 pages).
Exhibit 1015—Declaration of Peter Bliss in Support of Plaintiff's Opening Brief on Claim Construction, dated May 3, 2016, filed at the Patent Trial and Appeal Board on Nov. 18, 2016, Case No. IPR2017-00453 (10 pages).
Exhibit 1016—Plaintiff's Opening Claim Construction Brief, dated Jun. 3, 2016, filed at the Patent Trial and Appeal Board on Nov. 18, 2016, Case No. IPR2017-00453 (32 pages).
Exhibit 1017—Plaintiff's Responsive Claim Construction Brief, dated Jun. 24, 2016, filed at the Patent Trial and Appeal Board on Nov. 18, 2016, Case No. IPR2017-00453 (12 pages).
Exhibit 1020—U.S. Pat. No. 3,386,802 (Michalko), filed at the Patent Trial and Appeal Board on Nov. 18, 2016, Case No. IPR2017-00453 (6 pages).
Exhibit 1021—U.S. Pat. No. 4,094,775 (Mueller), filed at the Patent Trial and Appeal Board on Nov. 18, 2016, Case No. IPR2017-00453 (21 pages).
Exhibit 1022—U.S. Pat. No. 4,530,706 (Jones), filed at the Patent Trial and Appeal Board on Nov. 18, 2016, Case No. IPR2017-00453 (22 pages).
Exhibit 1023—U.S. Pat. No. 4,948,391(Noguchi), filed at the Patent Trial and Appeal Board on Nov. 18, 2016, Case No. IPR2017-00453 (18 pages).
Exhibit 1024—U.S. Pat. No. 5,001,289 (Nakano), filed at the Patent Trial and Appeal Board on Nov. 18, 2016, Case No. IPR2017-00453 (7 pages).
Exhibit 1025—U.S. Pat. No. 6,149,138 (Birdsell), filed at the Patent Trial and Appeal Board on Nov. 18, 2016, Case No. IPR2017-00453 (7 pages).
Exhibit 1026—U.S. Pat. No. 6,551,384 (Ackley), filed at the Patent Trial and Appeal Board on Nov. 18, 2016, Case No. IPR2017-00453 (13 pages).
Exhibit 1027—U.S. Pat. No. 6,651,658 (Hill), filed at the Patent Trial and Appeal Board on Nov. 18, 2016, Case No. IPR2017-00453 (17 pages).
Exhibit 1028—U.S. Pat. No. 6,755,895 (Lomax), filed at the Patent Trial and Appeal Board on Nov. 18, 2016, Case No. IPR2017-00453 (19 pages).
Exhibit 1029—U.S. Pat. No. 7,144,446 (Lessi), filed at the Patent Trial and Appeal Board on Nov. 18, 2016, Case No. IPR2017-00453 (4 pages).
Exhibit 1030—U.S. Pat. No. 7,828,878 (Zhong), filed at the Patent Trial and Appeal Board on Nov. 18, 2016, Case No. IPR2017-00453 (11 pages).
Exhibit 1031—U.S. Pat. No. 8,114,194 (Haggerty), filed at the Patent Trial and Appeal Board on Nov. 18, 2016, Case No. IPR2017-00453 (6 pages).
Exhibit 1032—U.S. Pat. No. 8,388,745 (Pelletier), filed at the Patent Trial and Appeal Board on Nov. 18, 2016, Case No. IPR2017-00453 (10 pages).
Exhibit 1033—U.S. Patent Publication No. 2004/0107831 (Graham), filed at the Patent Trial and Appeal Board on Nov. 18, 2016, Case No. IPR2017-00453 (19 pages).
Exhibit 1034—U.S. Patent Publication No. 2005/0045041 (Hechinger), filed at the Patent Trial and Appeal Board on Nov. 18, 2016, Case No. IPR2017-00453 (36 pages).
Exhibit 1035—U.S. Patent Publication No. 2005/0103341 (Deane), filed at the Patent Trial and Appeal Board on Nov. 18, 2016, Case No. IPR2017-00453 (46 pages).
Exhibit 1036—U.S. Patent Publication No. 2006/0000223 (Dickerson), filed at the Patent Trial and Appeal Board on Nov. 18, 2016, Case No. IPR2017-00453 (23 pages).
Exhibit 1038—U.S. Patent Publication No. 2009/0145428 (Sward), filed at the Patent Trial and Appeal Board on Nov. 18, 2016, Case No. IPR2017-00453 (37 pages).
Exhibit 1039—U.S. Patent Publication No. 2010/0196213 (Lutz), filed at the Patent Trial and Appeal Board on Nov. 18, 2016, Case No. IPR2017-00453 (20 pages).
Exhibit 1040—European Publication No. EP 0013680 (Earls), filed at the Patent Trial and Appeal Board on Nov. 18, 2016, Case No. IPR2017-00453 (35 pages).
Notice of Filing Date Accorded to Petition and Time for Filing Patent Owner Preliminary Response for Inter Partes Review of U.S. Pat. No. 8,894,751, issued the Patent Trial and Appeal Board on Dec. 7, 2016, Case No. IPR2017-00300 (5 pages).
Joint Stipulation to Amend Certain Pretrial Deadlines and Proposed Order filed on Jan. 23, 2017 by Separation Design Group IP Holdings, LLC, in the U.S. District Court for the Central District of California (*Separation Design Group IP Holdings, LLC* v. *Inogen, Inc.* // Case No. 2:15-cv-08323) (6 pages).
Joint Report on Settlement Status filed on Feb. 7, 2017 by Separation Design Group IP Holdings, LLC, in the U.S. District Court for the Central District of California (*Separation Design Group IP Holdings, LLC* v. *Inogen, Inc.* // Case No. 2:15-cv-08323) (4 pages).
Order Granting Joint Stipulation to Amend Certain Pretrial Deadlines dated Feb. 7, 2017 by Separation Design Group IP Holdings, LLC, in the U.S. District Court for the Central District of California (*Separation Design Group IP Holdings, LLC* v. *Inogen, Inc.* // Case No. 2:15-cv-08323) (2 pages).
Patent Owner's Mandatory Disclosures, filed by Separation Design Group IP Holdings, LLC, on Dec. 28, 2016, for Inter Partes Review of U.S. Pat. No. 9,199,055, filed at the Patent Trial and Appeal Board on Dec. 8, 2016, Case No. IPR2017-00453 (6 pages).
Patent Owner's Mandatory Disclosures, filed by Separation Design Group IP Holdings, LLC, on Dec. 9, 2016, for Inter Partes Review of U.S. Pat. No. 8,894,751, filed at the Patent Trial and Appeal Board on Nov. 18, 2016, Case No. IPR2017-00300 (6 pages).
Patent Owner's Preliminary Response, filed by Separation Design Group IP Holdings, LLC, on Mar. 7, 2017, for Inter Partes Review of U.S. Pat. No. 8,894,751, filed at the Patent Trial and Appeal Board on Nov. 18, 2016, Case No. IPR2017-00300 (58 pages).
Patent Owner's Preliminary Response, Ex. 2001, filed by Separation Design Group IP Holdings, LLC, on Mar. 7, 2017, for Inter Partes Review of U.S. Pat. No. 8,894,751, filed at the Patent Trial and Appeal Board on Nov. 18, 2016, Case No. IPR2017-00300 (26 pages).
Patent Owner's Preliminary Response, Ex. 2002, filed by Separation Design Group IP Holdings, LLC, on Mar. 7, 2017, for Inter Partes Review of U.S. Pat. No. 8,894,751, filed at the Patent Trial and Appeal Board on Nov. 18, 2016, Case No. IPR2017-00300 (19 pages).
Patent Owner's Preliminary Response, Ex. 2003, filed by Separation Design Group IP Holdings, LLC, on Mar. 7, 2017, for Inter

(56) References Cited

OTHER PUBLICATIONS

Partes Review of U.S. Pat. No. 8,894,751, filed at the Patent Trial and Appeal Board on Nov. 18, 2016, Case No. IPR2017-00300 (69 pages).
Patent Owner's Preliminary Response, Ex. 2004, filed by Separation Design Group IP Holdings, LLC, on Mar. 7, 2017, for Inter Partes Review of U.S. Pat. No. 8,894,751, filed at the Patent Trial and Appeal Board on Nov. 18, 2016, Case No. IPR2017-00300 (213 pages).
Patent Owner's Preliminary Response, Ex. 2005, filed by Separation Design Group IP Holdings, LLC, on Mar. 7, 2017, for Inter Partes Review of U.S. Pat. No. 8,894,751, filed at the Patent Trial and Appeal Board on Nov. 18, 2016, Case No. IPR2017-00300 (40 pages).
Patent Owner's Preliminary Response, Ex. 2006, filed by Separation Design Group IP Holdings, LLC, on Mar. 7, 2017, for Inter Partes Review of U.S. Pat. No. 8,894,751, filed at the Patent Trial and Appeal Board on Nov. 18, 2016, Case No. IPR2017-00300 (3 pages).
Patent Owner's Preliminary Response, Ex. 2007, filed by Separation Design Group IP Holdings, LLC, on Mar. 7, 2017, for Inter Partes Review of U.S. Pat. No. 8,894,751, filed at the Patent Trial and Appeal Board on Nov. 18, 2016, Case No. IPR2017-00300 (5 pages).
Patent Owner's Preliminary Response, Ex. 2008, filed by Separation Design Group IP Holdings, LLC, on Mar. 7, 2017, for Inter Partes Review of U.S. Pat. No. 8,894,751, filed at the Patent Trial and Appeal Board on Nov. 18, 2016, Case No. IPR2017-00300 (5 pages).
Patent Owner's Preliminary Response, Ex. 2009, filed by Separation Design Group IP Holdings, LLC, on Mar. 7, 2017, for Inter Partes Review of U.S. Pat. No. 8,894,751, filed at the Patent Trial and Appeal Board on Nov. 18, 2016, Case No. IPR2017-00300 (4 pages).
Patent Owner's Preliminary Response, Ex. 2010, filed by Separation Design Group IP Holdings, LLC, on Mar. 7, 2017, for Inter Partes Review of U.S. Pat. No. 8,894,751, filed at the Patent Trial and Appeal Board on Nov. 18, 2016, Case No. IPR2017-00300 (3 pages).
Patent Owner's Preliminary Response and Exhibits, filed by Separation Design Group IP Holdings, LLC, for Inter Partes Review of U.S. Pat. No. 9,199,055, filed at the Patent Trial and Appeal Board on Dec. 8, 2016, Case No. IPR2017-00453 (452 pages).
Inogen's Memoradum in Support of its Motion to Dismiss, filed by Inogen, Inc., on Mar. 20, 2017, in the U.S. District Court for the Central District of California (*Separation Design Group IP Holdings, LLC* v. *Inogen, Inc.* // Case No. 2:15-cv-08323) (15 pages).
Inogen's Motion to Dismiss, filed by Inogen, Inc., on Mar. 20, 2017, in the U.S. District Court for the Central District of California (*Separation Design Group IP Holdings, LLC* v. *Inogen, Inc.* // Case No. 2:15-cv-08323) (3 pages).
Declaration of Nicholas Zovko in Support of the Motion to Dismiss, filed by Separation Design Group IP Holdings, LLC, on Mar. 20, 2017, in the U.S. District Court for the Central District of California (*Separation Design Group IP Holdings, LLC* v. *Inogen, Inc.* // Case No. 2:15-cv-08323) (100 pages).
Declaration of Brenton Taylor in support of Inogen's Motion for Summary Judgment and supporting documents, filed by Inogen, Inc., on Mar. 20, 2017, in the U.S. District Court for the Central District of California (*Separation Design Group IP Holdings, LLC* v. *Inogen, Inc.* // Case No. 2:15-cv-08323) (95 pages).
Inogen's Motion for Summary Judgment and supporting documents, filed by Inogen, Inc., on Mar. 20, 2017, in the U.S. District Court for the Central District of California (*Separation Design Group IP Holdings, LLC* v. *Inogen, Inc.* // Case No. 2:15-cv-08323) (841 pages).
Declaration of Nicholas Zovko in Support of the Motion for Summary Judgment, filed by Separation Design Group IP Holdings, LLC, on Mar. 20, 2017, in the U.S. District Court for the Central District of California (*Separation Design Group IP Holdings, LLC* v. *Inogen, Inc.* // Case No. 2:15-cv-08323) (677 pages).
Inogen's Statement of Uncontroverted Facts in support of the Motion for Summary Judgment, filed by Inogen, Inc., on Mar. 20, 2017, in the U.S. District Court for the Central District of California (*Separation Design Group IP Holdings, LLC* v. *Inogen, Inc.* // Case No. 2:15-cv-08323) (32 pages).
Inogen's Memorandum in support of the Motion for Summary Judgment, filed by Inogen, Inc., on Mar. 20, 2017, in the U.S. District Court for the Central District of California (*Separation Design Group IP Holdings, LLC* v. *Inogen, Inc.* // Case No. 2:15-cv-08323) (31 pages).
Motion for Summary Judgment and supporting documents, filed by Separation Design Group IP Holdings, LLC, on Mar. 20, 2017, in the U.S. District Court for the Central District of California (*Separation Design Group IP Holdings, LLC* v. *Inogen, Inc.* // Case No. 2:15-cv-08323) (375 pages).
Declaration of Stephen G. Kunin in support of Inogen's Opposition to Plaintiff's Motion for Summary Judgment, filed by Inogen, Inc., on Mar. 20, 2017, in the U.S. District Court for the Central District of California (*Separation Design Group IP Holdings, LLC* v. *Inogen, Inc.* // Case No. 2:15-cv-08323) (33 pages).
Declaration of Brenton Taylor in support of Inogen's Motion for Summary Judgment and supporting documents, filed by Inogen, Inc., on Apr. 3, 2017, in the U.S. District Court for the Central District of California (*Separation Design Group IP Holdings, LLC* v. *Inogen, Inc.* // Case No. 2:15-cv-08323) (37 pages).
Inogen's Reply in Support of its Motion to Dismiss, filed on Apr. 10, 2017, in the U.S. District Court for the Central District of California (*Separation Design Group IP Holdings, LLC* v. *Inogen, Inc.* // Case No. 2:15-cv-08323) (13 pages).
Plaintiff's Reply in support of its Motion for Summary Judgment, filed by Separation Design Group IP Holdings, LLC, on Apr. 10, 2017, in the U.S. District Court for the Central District of California (*Separation Design Group IP Holdings, LLC* v. *Inogen, Inc.* // Case No. 2:15-cv-08323) (15 pages).
Declaration of Todd Blumenfeld in support of Plaintiff's Reply in support of its Motion for Summary Judgment, filed by Separation Design Group IP Holdings, LLC, on Apr. 10, 2017, in the U.S. District Court for the Central District of California (*Separation Design Group IP Holdings, LLC* v. *Inogen, Inc.* // Case No. 2:15-cv-08323) (18 pages).
Declaration of Wendy A. Choi in support of Plaintiff's Reply in support of its Motion for Summary Judgment, filed by Separation Design Group IP Holdings, LLC, on Apr. 10, 2017, in the U.S. District Court for the Central District of California (*Separation Design Group IP Holdings, LLC* v. *Inogen, Inc.* // Case No. 2:15-cv-08323) (288 pages).
Inogen's Reply in support of its Motion for Summary Judgment, filed by Inogen, Inc., on Apr. 10, 2017, in the U.S. District Court for the Central District of California (*Separation Design Group IP Holdings, LLC* v. *Inogen, Inc.* // Case No. 2:15-cv-08323) (15 pages).
Declaration of Nicholas Zovko in support of Inogen's Motion for Summary Judgment, filed by Inogen, Inc., on Apr. 10, 2017, in the U.S. District Court for the Central District of California (*Separation Design Group IP Holdings, LLC* v. *Inogen, Inc.* // Case No. 2:15-cv-08323) (23 pages).
Notice of Lodging PowerPoint slides in support of Inogen's Motion for Summary Judgment, filed by Inogen, Inc., on Apr. 25, 2017, in the U.S. District Court for the Central District of California (*Separation Design Group IP Holdings, LLC* v. *Inogen, Inc.* // Case No. 2:15-cv-08323) (99 pages).
Inogen's Opposition to Plaintiff's Motion for Summary Judgment filed on Apr. 25, 2017, in the U.S. District Court for the Central District of California (*Separation Design Group IP Holdings, LLC* v. *Inogen, Inc.* // Case No. 2:15-cv-08323) (31 pages).
Inogen's Statement of Genuine Disputes of Material Fact in support of is Opposition to Plaintiff's Motion for Summary Judgment, filed by Inogen, Inc., on Apr. 25, 2017, in the U.S. District Court for the Central District of California (*Separation Design Group IP Holdings, LLC* v. *Inogen, Inc.* // Case No. 2:15-cv-08323) (61 pages).

(56) References Cited

OTHER PUBLICATIONS

Plaintiff's Opposition to Inogen's Motion to Dismiss, filed by filed on Apr. 3, 2017, in the U.S. District Court for the Central District of California (*Separation Design Group IP Holdings, LLC v. Inogen, Inc.* // Case No. 2:15-cv-08323) (326 pages).
Plaintiff's Opposition to Inogen's Motion for Summary Judgment, filed on Apr. 3, 2017, in the U.S. District Court for the Central District of California (*Separation Design Group IP Holdings, LLC v. Inogen, Inc.* // Case No. 2:15-cv-08323) (118 pages).
Notice of Lodging PowerPoint slides tendered to the Court at the Apr. 24, 2017, Hearing on Inogen's Motion for Summary Judgment and cross Motions for Summary Judgment, filed by Separation Design Group IP Holdings, LLC., on Apr. 26, 2017, in the U.S. District Court for the Central District of California (*Separation Design Group IP Holdings, LLC v. Inogen, Inc.* // Case No. 2:15-cv-08323) (51 pages).
Notice of Lodging Notice of Motion and Motion for Summary Judgment and Exhibit filed by Inogen, Inc., on Apr. 26, 2017, in the U.S. District Court for the Central District of California (*Separation Design Group IP Holdings, LLC v. Inogen, Inc.* // Case No. 2:15-cv-08323) (48 pages).
Notice of Motion and Motion to Supplement Record for Pending Motions for Summary Judgment, Memorandum in Support, Declaration of Nicholas M. Zovko in Support, and Exhibits filed by Inogen, Inc. on Jun. 1, 2017, in the U.S. District Court for the Central District of California (*Separation Design Group IP Holdings, LLC v. Inogen, Inc.* // Case No. 2:15-cv-08323) (58 pages).
Notice of Motion and Motion to Stay Case Pending Inter Partes review, Memorandum in Support, Declaration of Nicholas M. Zovko in Support, and Exhibits filed by Inogen, Inc. on Jun. 1, 2017, in the U.S. District Court for the Central District of California (*Separation Design Group IP Holdings, LLC v. Inogen, Inc.* // Case No. 2:15-cv-08323) (371 pages).
Trial Instituted Document entered by the Board on May 19, 2017, for Inter Partes Review of U.S. Pat. No. 8,894,751, filed at the Patent Trial and Appeal Board on Nov. 18, 2016, Case No. IPR2017-00300 (35 pages).
Preliminary Response and Exhibits filed by Separation Design Group IP Holdings, LLC, on Apr. 4, 2017, for Inter Partes Review of U.S. Pat. No. 9,199,055, filed at the Patent Trial and Appeal Board on Dec. 8, 2016, Case No. IPR2017-00453 (452 pages).
Plaintiff's Objections to Evidence filed by Separation Design Group IP Holdings, LLC, on Jun. 5, 2017, for Inter Partes Review of U.S. Pat. No. 8,894,751, filed at the Patent Trial and Appeal Board on Nov. 18, 2016, Case No. IPR2017-00300 (7 pages).
Decision: Institution of Inter Partes Review entered by the Board on Jun. 16, 2017, for Inter Partes Review of U.S. Pat. No. 9,199,055, filed at the Patent Trial and Appeal Board on Dec. 8, 2016, Case No. IPR2017-00453 (32 pages).
Opposition re: Notice of Motion and Motion to Stay Case and Exhibits filed by Separation Deisgn Group IP Holdings LLC on Jun. 15, 2017, in the U.S. District Court for the Central District of California (*Separation Design Group IP Holdings, LLC v. Inogen, Inc.* // Case No. 2:15-cv-08323) (180 pages).
Declaration of Nicholas M. Zovko in Support of Inogen's Response re: Notice of Motion and Motion to Stay Case and Exhibits filed by Inogen, Inc., on Jun. 22, 2017, in the U.S. District Court for the Central District of California (*Separation Design Group IP Holdings, LLC v. Inogen, Inc.* // Case No. 2:15-cv-08323) (51 pages).
Patent Owner's Response to Petition Exhibits 2020-2024 for Inter Partes Review filed by Separation Design Group IP Holdings, LLC, on Aug. 21, 2017, for U.S. Pat. No. 8,894,751, which was filed at the Patent Trial and Appeal Board on Nov. 18, 2016; Case No. IPR2017-00300 (139 pages).
Patent Owner's Response to Petition Exhibit 2025 for Inter Partes Review filed by Separation Design Group IP Holdings, LLC, on Aug. 21, 2017, for U.S. Pat. No. 8,894,751, which was filed at the Patent Trial and Appeal Board on Nov. 18, 2016; Case No. IPR2017-00300 (323 pages).

Patent Owner's Response to Petition Exhibits 2026-2031, 2033, 2034, 2037, and 2040-2044 for Inter Partes Review filed by Separation Design Group IP Holdings, LLC, on Aug. 21, 2017, for U.S. Pat. No. 8,894,751, which was filed at the Patent Trial and Appeal Board on Nov. 18, 2016; Case No. IPR2017-00300 (260 pages).
Petitioner Inogen, Inc.'s Objections to Evidence Pursuant to 37 C.F.R. § 42.64(b)(1) filed by Inogen, Inc. on Aug. 29, 2017 for U.S. Pat. No. 8,894,751, which was filed at the Patent Trial and Appeal Board on Nov. 18, 2016; Case No. IPR2017-00300 (29 pages).
Order of Sealing Documents issued on Sep. 15, 2017 for U.S. Pat. No. 8,894,751, which was filed at the Patent Trial and Appeal Board on Nov. 18, 2016; Case No. IPR2017-00300 (7 pages).
Patent Owner's Response to Petition for Inter Partes Review filed at the Patent Trial and Appeal Board on Sep. 6, 2017, Case No. IPR2017-00453 (77 pages).
Exhibit 2013—The Growing Role of Human Factors and Usability Engineering for Medical Devices, filed at the Patent Trial and Appeal Board on Sep. 6, 2017, Case No. IPR2017-00453 (13 pages).
Exhibit 2016—Excerpt from File History of U.S. Patent Publication No. 2012/0266883 (Taylor)—Dec. 10, 2014 OA Response, filed at the Patent Trial and Appeal Board on Sep. 6, 2017, Case No. IPR2017-00453 (13 pages).
Exhibit 2017—U.S. Patent Publication 2006/0174874 (Jagger), filed at the Patent Trial and Appeal Board on Sep. 6, 2017, Case No. IPR2017-00453 (35 pages).
Order Re: Plaintiff's Motion for Summary Judgment on Inequitable Conduct, Infringement, and Prior Art entered by the Court on Jun. 2, 2017, in the U.S. District Court for the Central District of California (*Separation Design Group IP Holdings, LLC v. Inogen, Inc.* // Case No. 2:15-cv-08323) (10 pages).
Order Re: Defendants Motion for Summary Judgment, Non-Infringement and Invalidity entered by the Court on Jun. 1, 2017, in the U.S. District Court for the Central District of California (*Separation Design Group IP Holdings, LLC v. Inogen, Inc.* // Case No. 2:15-cv-08323) (9 pages).
Plaintiff's Opposition and Supporting Exhibits to Defendant's Motion to Stay Case Pending Inter Partes reviewfiled on Jun. 15, 2017, in the U.S. District Court for the Central District of California (*Separation Design Group IP Holdings, LLC v. Inogen, Inc.* // Case No. 2:15-cv-08323) (203 pages).
Defendant's Reply in Support of its Motion to Stay Case Pending Inter Partes review filed on Jun. 22, 2017, in the U.S. District Court for the Central District of California (*Separation Design Group IP Holdings, LLC v. Inogen, Inc.* // Case No. 2:15-cv-08323) (12 pages).
Order on Defendant's Motion to Dismiss Plaintiff's Infringement Claims for Lack of Standing entered by the Court on Jun. 2, 2017, in the U.S. District Court for the Central District of California (*Separation Design Group IP Holdings, LLC v. Inogen, Inc.* // Case No. 2:15-cv-08323) (6 pages).
Supplemental Declaration of Zovko in support of Defendant's Reply in Support of its Motion to Stay Case Pending Inter Partes review filed on Jun. 22, 2017, in the U.S. District Court for the Central District of California (*Separation Design Group IP Holdings, LLC v. Inogen, Inc.* // Case No. 2:15-cv-08323) (54 pages).
Order RE: Defendant's Motion to Stay Case Pending Inter Partes review issued on Jul. 11, 2017, in the U.S. District Court for the Central District of California (*Separation Design Group IP Holdings, LLC v. Inogen, Inc.* // Case No. 2:15-cv-08323) (6 pages).
Inogen's Objections to Evidence filed on Jun. 29, 2017, for Inter Partes Review of U.S. Pat. No. 9,199,055, filed at the Patent Trial and Appeal Board on Dec. 8, 2016, Case No. IPR2017-00453 (7 pages).
Declaration of Michael T. Cook, filed on Jul. 7, 2017, for Inter Partes Review of U.S. Pat. No. 9,199,055, filed at the Patent Trial and Appeal Board on Dec. 8, 2016, Case No. IPR2017-00453 (2 pages).
Patent Owner's Response to Petition, Exhibit List, and Exhibits 2013 and 2016-2019 for Inter Partes Review filed by Separation Design Group IP Holdings, LLC, on Aug. 21, 2017, for U.S. Pat. No. 8,894,751, which was filed at the Patent Trial and Appeal Board on Nov. 18, 2016; Case No. IPR2017-00300 (227 pages).

(56) References Cited

OTHER PUBLICATIONS

Exhibit 2018—Medical Device Use-Safety-Incorporating Human Factors Engineering 2000, filed at the Patent Trial and Appeal Board on Sep. 6, 2017, Case No. IPR2017-00453 (33 pages).
Exhibit 2019—Applying Human Factors and Usability Engineering to Medical Devices 2016, filed at the Patent Trial and Appeal Board on Sep. 6, 2017, Case No. IPR2017-00453 (49 pages).
Exhibit 2020—CDRH2O1461 HomeUseDesign FinalGuidance 2016, filed at the Patent Trial and Appeal Board on Sep. 6, 2017, Case No. IPR2017-00453 (27 pages).
Exhibit 2021—Releasable Definition and Meaning_Collins English Dictionary, filed at the Patent Trial and Appeal Board on Sep. 6, 2017, Case No. IPR2017-00453 (3 pages).
Exhibit 2022—American Heritage Dictionary Entry_Releasable, filed at the Patent Trial and Appeal Board on Sep. 6, 2017, Case No. IPR2017-00453 (2 pages).
Exhibit 2023—Guidance on Medical Device Patient Labeling 2001, filed at the Patent Trial and Appeal Board on Sep. 6, 2017, Case No. IPR2017-00453 (54 pages).
Exhibit 2024—Design Control Guidance for Medical Device manufacturers 1997, filed at the Patent Trial and Appeal Board on Sep. 6, 2017, Case No. IPR2017-00453 (53 pages).
Exhibit 2025—The Role of Human Factors in Home Health Care, filed at the Patent Trial and Appeal Board on Sep. 6, 2017, Case No. IPR2017-00453 (323 pages).
Exhibit 2026—medical Device Home Use Initiative, filed at the Patent Trial and Appeal Board on Sep. 6, 2017, Case No. IPR2017-00453 (10 pages).
Exhibit 2027—Recommendations for CLIA Waiver Apps for IVD Devices 2008, filed at the Patent Trial and Appeal Board on Sep. 6, 2017, Case No. IPR2017-00453 (44 pages).
Exhibit 2028—Age and Grip Strength Predict Hand Dexterity in Adults, filed at the Patent Trial and Appeal Board on Sep. 6, 2017, Case No. IPR2017-00453 (18 pages).
Exhibit 2029—Chronic Obstructive Pulmonary Disease—Cleveland Clinic, filed at the Patent Trial and Appeal Board on Sep. 6, 2017, Case No. IPR2017-00453 (22 pages).
Exhibit 2030—Product Review of Inogen One G2 and G3, filed at the Patent Trial and Appeal Board on Sep. 6, 2017, Case No. IPR2017-00453 (4 pages).
Exhibit 2031—Excerpt from File History of U.S. Patent Publication No. 2012/0266883 (Taylor)—Nov. 27, 2014 OA Response, filed at the Patent Trial and Appeal Board on Sep. 6, 2017, Case No. IPR2017-00453 (12 pages).
Exhibit 2033—Inogen One G3 Replacement Column Pair, filed at the Patent Trial and Appeal Board on Sep. 6, 2017, Case No. IPR2017-00453 (3 pages).
Exhibit 2034—Keeping Your Portable Concentrator in Top Condition, filed at the Patent Trial and Appeal Board on Sep. 6, 2017, Case No. IPR2017-00453 (2 pages).
Exhibit 2037—Vbox Trooper Brochure, filed at the Patent Trial and Appeal Board on Sep. 6, 2017, Case No. IPR2017-00453 (1 pages).
Exhibit 2040—Sprinkle Declaration, filed at the Patent Trial and Appeal Board on Sep. 6, 2017, Case No. IPR2017-00453 (77 pages).
Exhibit 2041—Sprinkle CV, filed at the Patent Trial and Appeal Board on Sep. 6, 2017, Case No. IPR2017-00453 (4 pages).
Exhibit 2042—Gosbee Declaration, filed at the Patent Trial and Appeal Board on Sep. 6, 2017, Case No. IPR2017-00453 (32 pages).
Exhibit 2043—Gosbee_John_CV, filed at the Patent Trial and Appeal Board on Sep. 6, 2017, Case No. IPR20717-00,71.53 (24 pages).
Exhibit 2044—Excerpts from U.S. Appl. No. 1487613, filed at the Patent Trial and Appeal Board on Sep. 6, 2017, Case No. IPR2017-00453 (29 pages).
Exhibit 2045—Second Declaration of Brett Pinkus, filed at the Patent Trial and Appeal Board on Sep. 6, 2017, Case No. IPR2017-00453 (7 pages).
Petitioner's Objections to Evidence Pursuant to 37 C.F.R. Sec. 42.64(b)(1), filed at the Patent Trial and Appeal Board on Sep. 13, 2017, Case No. IPR2017-00453 (24 pages).
Order to Seal Documents issued from the Patent Trial and Appeal Board on Sep. 15, 2017, Case No. IPR2017-00453 (7 pages).
Preliminary Amendment filed on Oct. 6, 2015 for U.S. Appl. No. 14/876,133, filed Oct. 6, 2015 and published as US-2016/0022951 on Jan. 28, 2016 (Inventor—Galbraith // Applicant—Separation Design Group, LLC) (8 pages).
Non-Final Office Action dated Nov. 9, 2016 for U.S. Appl. No. 14/876,133, filed Oct. 6, 2015 and published as US-2016/0022951 on Jan. 28, 2016 (Inventor—Galbraith // Applicant—Separation Design Group, LLC) ) (5 pages).
Terminal Disclaimer and Amendment to Non-Final Office Action filed on Apr. 17, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (5 pages).
Terminal Disclaimer Review Decision issued on May 4, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (1 page).
Final Office Action dated Jun. 7, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (6 pages).
Terminal Disclaimer and Amendment After Final Office Action filed on Jun. 14, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (3 pages).
Terminal Disclaimer Review Decision issued on Jun. 14, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (1 page).
Terminal Disclaimer and Amendment After Final Office Action filed on Jun. 21, 2017 for U.S. Appl. No. 14/876,133, filed on Oct. 6, 2015 and published as US-2016/0022951 on Jan. 28, 2016 (Inventor—Galbraith // Applicant—Separation Design Group, LLC) ) (3 pages).
Terminal Disclaimer Review Decision issued on Jun. 21, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (1 page).
Notice of Allowance dated Jun. 26, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (7 pages).
Amendment and Request for Continued Examination filed on Jun. 29, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (13 pages).
Preliminary Amendment filed on Jul. 18, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (10 pages).
Non-Final Office Action dated Aug. 16, 2017 for U.S. Appl. No. 14/876,133, filed Oct. 6, 2015 and published as US-2016/0022951 on Jan. 28, 2016 (Inventor—Galbraith // Applicant—Separation Design Group, LLC) ) (8 pages).
Terminal Disclaimer and Amendment to Non-Final Office Action filed on Aug. 25, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (12 pages).
Terminal Disclaimer Review Decision issued on Aug. 29, 2017 for U.S. Appl. No. 14/876,133, filed Oct. 6, 2015 and published as US-2016/0022951 on Jan. 28, 2016 (Inventor—Galbraith // Applicant—Separation Design Group, LLC) (1 page).
U.S. Appl. No. 61/264,069, filed Nov. 24, 2009, Stephen D. Galbraith (Separation Design IP Holdings, LLC).
U.S. Appl. No. 61/248,712, filed Oct. 5, 2009, Stephen D. Galbraith (Separation Design IP Holdings, LLC).
U.S. Appl. No. 13/499,943 (U.S Pat. No. 8,894,751), filed Apr. 3, 2012 (Nov. 25, 2014), Stephen D. Galbraith (Separation Design IP Holdings, LLC).

(56) References Cited

OTHER PUBLICATIONS

U.S. Appl. No. 14/519,868 (U.S. Pat. No. 9,199,055), filed Oct. 21, 2014, (Dec. 1, 2015), Stephen D. Galbraith (Separation Design IP Holdings, LLC).
U.S. Appl. No. 14/876,133 (2016/0022951), filed Oct. 6, 2015, (Jan. 28, 2016) Stephen D. Galbraith (Separation Design IP Holdings, LLC).
EP, 10822515.2 (2485794), Oct. 5, 2010 (Aug. 15, 2012), Stephen D. Galbraith (Separation Design IP Holdings, LLC).
PCT, PCT/US2010/051419 (WO 2011/044091), Oct. 5, 2010 (Apr. 14, 2011), Stephen D. Galbraith (Separation Design IP Holdings, LLC).
Plaintiff's Memorandum of Contentions of Fact and Law filed by Plaintiff Separation Design Group IP Holdings LLC on Oct. 2, 2017 in the U.S. District Court for the Central District of California (*Separation Design Group IP Holdings, LLC v. Inogen, Inc.* // Case No. 2:15-cv-08323) (44 pages).
Memorandum of Contentions of Fact and Law filed by Defendant Inogen, Inc. on Oct. 2, 2017 in the U.S. District Court for the Central District of California (*Separation Design Group IP Holdings, LLC v. Inogen, Inc.* // Case No. 2:15-cv-08323) (32 pages).
Notice of Motion and Motion to Clarify Court's Claim Construction Order filed by Plaintiff Separation Design Group IP Holdings LLC on Oct. 4, 2017 in the U.S. District Court for the Central District of California (*Separation Design Group IP Holdings, LLC v. Inogen, Inc.* // Case No. 2:15-cv-08323) (13 pages).
Ex Parte Application to Clarify Court's Claim Construction Order filed by Plaintiff Separation Design IP Holdings LLC on Oct. 4, 2017 in the U.S. District Court for the Central District of California (*Separation Design Group IP Holdings, LLC v. Inogen, Inc.* // Case No. 2:15-cv-08323) (9 pages).
Order Re: Plaintiff's Notice and Ex Parte Application to Shorten Time to Hear and Expedite Briefing for Its Motion to Clarify the Court's Claim Construction Order entered on Oct. 5, 2017 in the U.S. District Court for the Central District of California (*Separation Design Group IP Holdings, LLC v. Inogen, Inc.* // Case No. 2:15-cv-08323) (2 pages).
Notice of Motion and Motion in Limine to Preclude Testimony Related Solely to Defendant's Inequitable Conduct Allegations filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (8 pages).
Notice of Motion and Motion in Limine to Preclude Reference that Asserted Claims Were Written to Cover the Accused Products filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (7 pages).
Notice of Motion and Motion in Limine to Preclude Evidence or Argument that Replaceable by a User Can Be Met If Only the Most Technically Proficient of Users Can Remove the Adsorbent Module filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (8 pages).
Notice of Motion and Motion in Limine to Preclude Reference to Pelletier or Other Post-Dated references Not Established as Prior Art filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (7 pages).
Notice of Motion and Motion in Limine to Preclude Testimony Related to the Funding of the Litigation, Litigation Counsel, and the Division of Any Proceeds filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (20 pages).
Notice of Motion and Motion in Limine to Preclude Any Reference to Discovery Objections and Any Assertion by Plaintiff of Attorney/Client Privilege or work Product Immunity filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (7 pages).
Notice of Motion and Motion in Limine to Limit the Prior Art and Combinations of Prior Art filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (6 pages).
Notice of Motion and Motion in Limine to Preclude Any Evidence of Defendant's Defenses of Laches and Equitable Estoppel filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (9 pages).
Application to File Document Plaintiff's Motion in Limine No. 9 Under Seal and Exhibits A and B filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (59 pages).
Application to File Document Redacted Exhibit B to Todd I. Blumenfeld's Declaration in Support of Plaintiff's Motion to Strike Under Seal filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (7 pages).
Notice of Motion and Motion to Strike Certain Portions of Defendant Inogen Inc.'s Proffered Expert Testimony of Mr. David Hanson and Exhibits filed by Plaintiff Separation Design IP Holdings LLC on Oct. 6, 2017 in the U.S. District Court for the Central District of California (*Separation Design Group IP Holdings, LLC v. Inogen, Inc.* // Case No. 2:15-cv-08323) (48 pages).
Notice of Motion and Motion in Limine to Exclude Evidence, Testimony, Argument, or Description of Non-Asserted Trade Secrets filed by Defendant Inogen, Inc. on Oct. 6, 2017 in the U.S. District Court for the Central District of California (*Separation Design Group IP Holdings, LLC v. Inogen, Inc.* // Case No. 2:15-cv-08323) (7 pages).
Memorandum in Support of Motion in Limine to Exclude Evidence, Testimony, Argument, or Description of Non-Asserted Trade Secrets filed by Defendant Inogen, Inc. on Oct. 6, 2017 in the U.S. District Court for the Central District of California (*Separation Design Group IP Holdings, LLC v. Inogen, Inc.* // Case No. 2:15-cv-08323) (14 pages).
Notice of Motion and Motion in Limine to Exclude All Evidence, Testimony, Argument of Alleged "Confidential Information" and Improper Contract Arguments filed by Defendant Inogen, Inc. on Oct. 6, 2017 in the U.S. District Court for the Central District of California (*Separation Design Group IP Holdings, LLC v. Inogen, Inc.* // Case No. 2:15-cv-08323) (2 pages).
Memorandum in Support of Motion in Limine to Exclude All Evidence, Testimony, or Argument of Alleged "Confidential Information" and Improper Contract Arguments filed by Defendant Inogen, Inc. on Oct. 6, 2017 in the U.S. District Court for the Central District of California (*Separation Design Group IP Holdings, LLC v. Inogen, Inc.* // Case No. 2:15-cv-08323) (5 pages).
Notice of Motion and Motion in Limine to Exclude New, Contradictory, and Untimely Claim Constructions and "Interpretations" filed by Defendant Inogen, Inc. on Oct. 6, 2017 in the U.S. District Court for the Central District of California (*Separation Design Group IP Holdings, LLC v. Inogen, Inc.* // Case No. 2:15-cv-08323) (2 pages).
Memorandum in Support of Motion in Limine to Exclude New, Contradictory, and Untimely Claim Constructions and "Interpretations" filed by Defendant Inogen, Inc. on Oct. 6, 2017 in the U.S. District Court for the Central District of California (*Separation Design Group IP Holdings, LLC v. Inogen, Inc.* // Case No. 2:15-cv-08323) (6 pages).
Notice of Motion and Motion in Limine to Exclude SDG's Witnesses from Testifying as to Alleged Credibility or Bias of Inogen Witnesses filed by Defendant Inogen, Inc. on Oct. 6, 2017 in the

(56) References Cited

OTHER PUBLICATIONS

U.S. District Court for the Central District of California (*Separation Design Group IP Holdings, LLC* v. *Inogen, Inc.* // Case No. 2:15-cv-08323) (2 pages).

Memorandum in Support of Motion in Limine to Exclude SDG's Witnesses from Testifying as to Alleged Credibility or Bias of Inogen Witnesses filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (3 pages).

Notice of Motion and Motion in Limine to Exclude Reference to the Financial Condition of Inogen before 2009 filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (2 pages).

Memorandum in Support of Motion in Limine to Exclude Reference to the Financial Condition of Inogen before 2009 filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (4 pages).

Notice of Motion and Motion in Limine to Exclude as Trial Exhibits SDG's Litigation-Generated Tables for Alleged Non-Disclosure and Employment Agreements filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (2 pages).

Memorandum in Support of Motion in Limine to Exclude as Trial Exhibits SDG's Litigation-Generated Tables for Alleged Non-Disclosure and Employment Agreements filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (4 pages).

Notice of Motion and Motion in Limine to Exclude Testimony, Evidence, or Argument Regarding Hearsay by Non-Parties filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (2 pages).

Memorandum in Support of Motion in Limine to Exclude Testimony, Evidence, or Argument Regarding Hearsay by Non-Parties filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (5 pages).

Notice of Motion and Motion in Limine to Exclude Testimony of William Hooper, M.D. filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (2 pages).

Memorandum in Support of Motion in Limine to Exclude Testimony of William Hooper, M.D. filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (4 pages).

Notice of Motion and Motion in Limine to Exclude All Evidence, Argument, and Testimony Regarding "Google Analytics" filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (2 pages).

Memorandum in Support of Motion in Limine to Exclude All Evidence, Argument, and Testimony Regarding "Google Analytics" filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (4 pages).

Notice of Motion and Motion in Limine to Exclude All Evidence, Argument, and Testimony Regarding Human Factors Engineering filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (2 pages).

Memorandum in Support of Motion in Limine to Exclude All Evidence, Argument, and Testimony Regarding Human Factors Engineering filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (5 pages).

Notice of Motion and Motion in Limine to Exclude Testimony Regarding Unrelated Large Companies, Such as Apple, Yahoo, and Pfizer filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (2 pages).

Memorandum in Support of Motion in Limine to Exclude Testimony Regarding Unrelated Large Companies, Such as Apple, Yahoo, and Pfizer filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (6 pages).

Notice of Motion and Motion in Limine to Preclude Admission of Third-Party License Agreements filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (2 pages).

Memorandum in Support of Motion in Limine to Preclude Admission of Third-Party License Agreements filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (4 pages).

Notice of Motion and Motion in Limine to Exclude Confidentiality Designations Added for this Lawsuit Pursuant to the Protective Order filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (2 pages).

Memorandum in Support of Motion in Limine to Exclude Confidentiality Designations Added for this Lawsuit Pursuant to the Protective Order filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (4 pages).

Notice of Motion and Motion in Limine to Exclude Incomplete Categories of Documents and Untimely Expert Reports filed by Defendant Inogen, Inc. on Oct. 6, 2017 in the U.S. District Court for the Central District of California (*Separation Design Group IP Holdings, LLC* v. *Inogen, Inc.* // Case No. 2:15-cv-08323) (2 pages).

Declaration of Nicole R. Townes in Support of Motion in Limine to Exclude All Evidence, Testimony or Argument of Alleged "Confidential Information" and Improper Contract Arguments filed by Defendant Inogen, Inc. on Oct. 7, 2017 in the U.S. District Court for the Central District of California (*Separation Design Group IP Holdings, LLC* v. *Inogen, Inc.* // Case No. 2:15-cv-08323) (13 pages).

Memorandum in Support of Motion in Limine to Exclude Incomplete Categories of Documents and Untimely Expert Reports filed by Defendant Inogen, Inc. on Oct. 7, 2017 in the U.S. District Court for the Central District of California (*Separation Design Group IP Holdings, LLC* v. *Inogen, Inc.* // Case No. 2:15-cv-08323) (7 pages).

Application to File Document Memorandum in Support of Motion in Limine No. 14 and certain Exhibits in Support of Motions in Limine Nos. 1-14 Under Seal filed by Defendant Inogen, Inc. on Oct. 7, 2017 in the U.S. District Court for the Central District of California (*Separation Design Group IP Holdings, LLC* v. *Inogen, Inc.* // Case No. 2:15-cv-08323) (13 pages).

Notice of Motion and Motion to Strike and Exclude Opinions and Testimony of Plaintiff's Expert Michael Pellegrino filed by Defendant Inogen, Inc. on Oct. 7, 2017 in the U.S. District Court for the Central District of California (*Separation Design Group IP Holdings, LLC* v. *Inogen, Inc.* // Case No. 2:15-cv-08323) (2 pages).

Memorandum in Support of Notice of Motion and Motion to Strike and Exclude Opinions and Testimony of Plaintiff's Expert Michael Pellegrino filed by Defendant Inogen, Inc. on Oct. 7, 2017 in the

(56) References Cited

OTHER PUBLICATIONS

U.S. District Court for the Central District of California (*Separation Design Group IP Holdings, LLC* v. *Inogen, Inc.* // Case No. 2:15-cv-08323) (30 pages).
Notice of Motion and Motion to Strike and Exclude Opinions and Testimony of Plaintiff's Expert Thomas Sprinkle filed by Defendant Inogen, Inc. on Oct. 7, 2017 in the U.S. District Court for the Central District of California (*Separation Design Group IP Holdings, LLC* v. *Inogen, Inc.* // Case No. 2:15-cv-08323) (2 pages).
Memorandum in Support of Notice of Motion and Motion to Strike and Exclude Opinions and Testimony of Plaintiffs Expert Thomas Sprinkle filed by Defendant Inogen, Inc. on Oct. 7, 2017 in the U.S. District Court for the Central District of California (*Separation Design Group IP Holdings, LLC* v. *Inogen, Inc.* // Case No. 2:15-cv-08323) (26 pages).
Declaration of Nicole R. Townes in Support of Notice of Motion and Motion to Strike and Exclude Opinions and Testimony of Plaintiff's Expert Thomas Sprinkle and Exhibits filed by Defendant Inogen, Inc. on Oct. 7, 2017 in the U.S. District Court for the Central District of California (*Separation Design Group IP Holdings, LLC* v. *Inogen, Inc.* // Case No. 2:15-cv-08323) (118 pages).
Proposed Voir Dire Questions filed by Plaintiff Separation Design IP Holdings LLC on Oct. 10, 2017 in the U.S. District Court for the Central District of California (*Separation Design Group IP Holdings, LLC* v. *Inogen, Inc.* // Case No. 2:15-cv-08323) (6 pages).
Statement—Joint Statement of the Case filed by Plaintiff Separation Design IP Holdings LLC on Oct. 10, 2017 in the U.S. District Court for the Central District of California (*Separation Design Group IP Holdings, LLC* v. *Inogen, Inc.* // Case No. 2:15-cv-08323) (7 pages).
Witness List filed by Plaintiff Separation Design IP Holdings LLC on Oct. 10, 2017 in the U.S. District Court for the Central District of California (*Separation Design Group IP Holdings, LLC* v. *Inogen, Inc.* // Case No. 2:15-cv-08323) (15 pages).
Joint Exhibit List and Notice of Disputed Exhibits Exhibit List filed by Plaintiff Separation Design IP Holdings LLC on Oct. 10, 2017 in the U.S. District Court for the Central District of California (*Separation Design Group IP Holdings, LLC* v. *Inogen, Inc.* // Case No. 2:15-cv-08323) (123 pages).
Proposed Voir Dire Questions filed by Defendant Inogen, Inc. on Oct. 10, 2017 in the U.S. District Court for the Central District of California (*Separation Design Group IP Holdings, LLC* v. *Inogen, Inc.* // Case No. 2:15-cv-08323) (5 pages).
Notice of Lodging Proposed Pretrial Conference Order Defendant Inogen, Inc. filed on Oct. 10, 2017 in the U.S. District Court for the Central District of California (*Separation Design Group IP Holdings, LLC* v. *Inogen, Inc.* // Case No. 2:15-cv-08323) (55 pages).
Competing Verdict Forms filed by Defendant Inogen, Inc. on Oct. 10, 2017 in the U.S. District Court for the Central District of California (*Separation Design Group IP Holdings, LLC* v. *Inogen, Inc.* // Case No. 2:15-cv-08323) (48 pages).
Proposed Jury Instructions filed by Defendant Inogen, Inc. on Oct. 10, 2017 in the U.S. District Court for the Central District of California (*Separation Design Group IP Holdings, LLC* v. *Inogen, Inc.* // Case No. 2:15-cv-08323) (122 pages).
Order to Strike Electronically Filed Documents by Judge John A. Kronstadt filed on Oct. 10, 2017 in the U.S. District Court for the Central District of California (*Separation Design Group IP Holdings, LLC* v. *Inogen, Inc.* // Case No. 2:15-cv-08323) (1 page).
Second Request to File Document Redacted Exhibit B to Todd I. Blumenfeld's Declaration in Support of Plaintiff's Motion to Strike Under Seal filed by Plaintiff Separation Design IP Holdings LLC on Oct. 11, 2017 in the U.S. District Court for the Central District of California (*Separation Design Group IP Holdings, LLC* v. *Inogen, Inc.* // Case No. 2:15-cv-08323) (9 pages).
Notice to Filer of Deficiencies in Electronically Filed Documents Re: Second Request to File Document Redacted Exhibit B to Todd I. Blumenfeld's Declaration in Support of Plaintiff's Motion to Strike Under Seal filed on Oct. 12, 2017 in the U.S. District Court for the Central District of California (*Separation Design Group IP Holdings, LLC* v. *Inogen, Inc.* // Case No. 2:15-cv-08323) (1 page).

Notice of Lodging filed of Proposed Order Granting Re: Second Request to File Document Redacted Exhibit B to Todd I. Blumenfeld's Declaration in Support of Plaintiff's Motion to Strike Under Seal entered on Oct. 12, 2017 in the U.S. District Court for the Central District of California (*Separation Design Group IP Holdings, LLC* v. *Inogen, Inc.* // Case No. 2:15-cv-08323) (4 pages).
Order Re: Inogen's Applications to File Under Seal entered on Oct. 12, 2017 in the U.S. District Court for the Central District of California (*Separation Design Group IP Holdings, LLC* v. *Inogen, Inc.* // Case No. 2:15-cv-08323) (3 pages).
Order Re: Plaintiff's Second Request to File Exhibit B to Declaration Todd I. Blumenfeld in Support of Plaintiff's Motion to Strike Portions of Defendant Inogen, Inc.'s Proffered Expert Testimony of David Hanson entered on Oct. 13, 2017 in the U.S. District Court for the Central District of California (*Separation Design Group IP Holdings, LLC* v. *Inogen, Inc.* // Case No. 2:15-cv-08323) (2 pages).
Memorandum in Opposition to Motion to Clarify Court's Claim Construction Order filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (11 pages).
Memorandum in Opposition to Notice of Motion and Motion to Strike Certain Portions of Defendant Inogen, Inc.'s Proffered Expert Testimony of Mr. David Hanson filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (14 pages).
Opposition Plaintiff Separation Design Group IP Holdings, LLC's Response to Defendant Inogen, Inc.'s Motion in Limine No. 1 filed by Plaintiff Separation Design Group IP Holdings, LLC on Oct. 10, 2017 in the U.S. District Court for the Central District of California (*Separation Design Group IP Holdings, LLC* v. *Inogen, Inc.* // Case No. 2:15-cv-08323) (8 pages).
Opposition Plaintiff Separation Design Group IP Holdings, LLC's Response to Defendant Inogen, Inc.'s Motion in Limine No. 2 filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (6 pages).
Opposition Plaintiff Separation Design Group IP Holdings, LLC's Response to Defendant Inogen, Inc.'s Motion in Limine No. 3 filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (6 pages).
Opposition Plaintiff Separation Design Group IP Holdings, LLC's Response to Defendant Inogen, Inc.'s Motion in Limine No. 4 filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (3 pages).
Opposition Plaintiff Separation Design Group IP Holdings, LLC's Response to Defendant Inogen, Inc.'s Motion in Limine No. 5 filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (7 pages).
Opposition Plaintiff Separation Design Group IP Holdings, LLC's Response to Defendant Inogen, Inc.'s Motion in Limine No. 6 filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (4 pages).
Opposition Plaintiff Separation Design Group IP Holdings, LLC's Response to Defendant Inogen, Inc.'s Motion in Limine No. 7 filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (4 pages).
Opposition Plaintiff Separation Design Group IP Holdings, LLC's Response to Defendant Inogen, Inc.'s Motion in Limine No. 9 filed by Plaintiff Separation Design Group IP Holdings, LLC on Oct. 16,

(56) References Cited

OTHER PUBLICATIONS 2017 in the U.S. District Court for the Central District of California (*Separation Design Group IP Holdings, LLC* v. *Inogen, Inc.* // Case No. 2:15-cv-08323) (6 pages).
Opposition Plaintiff Separation Design Group IP Holdings, LLC's Response to Defendant Inogen, Inc.'s Motion in Limine No. 11 filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (5 pages).
Opposition Plaintiff Separation Design Group IP Holdings, LLC's Response to Defendant Inogen, Inc.'s Motion in Limine No. 12 filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (5 pages).
Opposition Plaintiff Separation Design Group IP Holdings, LLC's Response to Defendant Inogen, Inc.'s Motion in Limine No. 13 filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (5 pages).
Opposition Plaintiff Separation Design Group IP Holdings, LLC's Response to Defendant Inogen, Inc.'s Motion in Limine No. 14 filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (11 pages).
Opposition to Notice of Motion and Motion to Strike and Exclude Opinions and Testimony of Plaintiff's Expert Thomas Sprinkle filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (20 pages).
Opposition to Notice of Motion and Motion to Strike and Exclude Opinions and Testimony of Plaintiff's Expert Michael Pellegrino filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (45 pages).
Application to File Document Exhibit A to Response to Motion to Strike and Exclude Opinions and Testimony of Plaintiff's Expert Michael Pellegrino Under Seal filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (24 pages).
Declaration of Nicole R. Townes in Opposition to Motion in Limine to Preclude Reference to Pelletier or Other Post-dated References Not Established as Prior Art, Motion in Limine to Preclude Reference to IPR Proceedings, Motion in Limine to Preclude Testimony Related Solely to Defendant's Inequitable Conduct Allegations, Motion in Limine to Preclude Reference that Asserted Claims Were Written to Cover the Accused Products, Motion in Limine to Preclude Evidence of Defendant's Defenses of Laches and Equitable Estoppel, Motion in Limine to Preclude Any Reference to Discovery Objections and Any Assertion by Plaintiff of Attorney/Client Privilege or Work Product Immunity, Notice of Motion and Motion to Strike certain Portions of Defendant Inogen, Inc.'s Proffered Expert Testimony of My. David Hanson, Motion in Limine to Preclude Evidence or Argument that Replaceable by a User Can Be Met If Only the Most Technically Proficient of Users Can remove the Adsorbent Module, Motion in Limine to Preclude Testimony Related to the Funding of this Litigation, Litigation Counsel, and the Division of Any Proceeds, Application to File Document Plaintiff's Motion in Limine No. 9 Under Seal, Motion in Limine to Limit the Prior Art and Combinations of Prior Art filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (6 pages).
Memorandum in Opposition to Motion in Limine to Preclude Testimony Related solely to Defendant's Inequitable conduct Allegations filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (7 pages).
Memorandum in Opposition to Motion in Limine to Preclude Reference that Asserted Claims Were Written to Cover the Accused Products filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (6 pages).
Memorandum in Opposition to Motion in Limine to Preclude Evidence or Argument that Replaceable by a User Can Be Met If Only the Most Technically Proficient of Users Can remove the Adsorbent Module filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (7 pages).
Memorandum in Opposition to Motion in Limine to Preclude Reference to Pelletier or Other Post-Dated References Not Established as Prior Art filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (4 pages).
Opposition to Motion in Limine to Exclude Testimony of William Hooper, M.D. filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (54 pages).
Memorandum in Opposition to Motion in Limine to Preclude Testimony Related to the Funding of this Litigation, Litigation Counsel, and the Division of Any Proceeds filed by by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (6 pages).
Application to File Exhibit D to Response to Inogen's Motion in Limine No. 8 to Exclude the Testimony of Dr. William Hooper, MD Under Seal filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (13 pages).
Opposition to Motion in Limine to Exclude All Evidence, Argument, and Testimony Regarding Human Factors Engineering filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (28 pages).
Memorandum in Opposition to Motion in Limine to Preclude Any Reference to Discovery Objections and Any Assertion by Plaintiff of Attorney/Client Privilege or Work Product Immunity filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (4 pages).
Application to File Document Exhibits A and B to Response to Inogen's Motion in Limine No. 10 Under Seal filed by Plaintiff Separation Design Group IP Holdings, LLC on Oct. 16, 2017 in the U.S. District Court for the Central District of California (*Separation Design Group IP Holdings, LLC* v. *Inogen, Inc.* // Case No. 2:15-cv-08323) (25 pages).
Memorandum in Opposition to Motion in Limine to Preclude Reference to IPR Proceedings filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (6 pages).
Memorandum in Opposition to Motion in Limine to Limit the Prior Art and Combinations of Prior Art filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (4 pages).

(56) References Cited

OTHER PUBLICATIONS

Memorandum of Points and Authorities in Opposition filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (5 pages).

Memorandum in Opposition to Motion in Limine to Preclude Evidence of Defendant's Defenses of Laches and Equitable Estoppel filed by Defendant Inogen, Inc. on Oct. 16, 2017 in the U.S. District Court for the Central District of California (*Separation Design Group IP Holdings, LLC* v. *Inogen, Inc.* // Case No. 2:15-cv-08323) (7 pages).

Renewed Application to File Document Under Seal filed by Defendant Inogen, Inc. on Oct. 17, 2017 in the U.S. District Court for the Central District of California (*Separation Design Group IP Holdings, LLC* v. *Inogen, Inc.* // Case No. 2:15-cv-08323) (9 pages).

Declaration of Nicole R. Townes in Support of renewed Application to File Document Under Seal filed by Defendant Inogen, Inc. on Oct. 17, 2017 in the U.S. District Court for the Central District of California (*Separation Design Group IP Holdings, LLC* v. *Inogen, Inc.* // Case No. 2:15-cv-08323) (209 pages).

Declaration of Brenton Taylor in Support of Renewed Application to File Document Under Seal filed by Defendant Inogen, Inc. on Oct. 17, 2017 in the U.S. District Court for the Central District of California (*Separation Design Group IP Holdings, LLC* v. *Inogen, Inc.* // Case No. 2:15-cv-08323) (7 pages).

Notice of Settlement filed by Defendant Inogen, Inc. on Oct. 18, 2017 in the U.S. District Court for the Central District of California (*Separation Design Group IP Holdings, LLC* v. *Inogen, Inc.* // Case No. 2:15-cv-08323) (2 pages).

Declaration of Nicole R. Townes in Support of Application to file Document Redacted Exhibit B to Todd I. Blumenfeld's Declaration in Support of Plaintiff's Motion to Strike Under Seal, Application to File Document Plaintiff's Motion in Limine No. 9 Under Seal filed by Defendant on Oct. 18, 2017 in the U.S. District Court for the Central District of California (*Separation Design Group IP Holdings, LLC* v. *Inogen, Inc.* // Case No. 2:15-cv-08323) (10 pages).

Declaration of Brenton Taylor in Support of Application to File Document Redacted Exhibit B to Todd I. Blumenfeld's Declaration in Support of Plaintiff's Motion to Strike Under Seal, Application to File Document Plaintiff's Motion in Limine No. 9 Under Seal filed by Defendant on Oct. 18, 2017 in the U.S. District Court for the Central District of California (*Separation Design Group IP Holdings, LLC* v. *Inogen, Inc.* // Case No. 2:15-cv-08323) (4 pages).

\* cited by examiner

ULTRA RAPID CYCLE PORTABLE OXYGEN CONCENTRATOR

CROSS-REFERENCE TO RELATED APPLICATIONS

This application is a continuation of U.S. application Ser. No. 14/876,133, currently pending, filed Oct. 6, 2015, which is a continuation of U.S. application Ser. No. 14/519,868 filed Oct. 21, 2014, now U.S. Pat. No. 9,199,055 issued Dec. 1, 2015, which is a continuation of U.S. application Ser. No. 13/499,943 filed Apr. 3, 2012, now U.S. Pat. No. 8,894,751 issued Nov. 25, 2014, which is a U.S. national phase patent application under 35 U.S.C. § 371 of International Patent Application No. PCT/US2010/51419 filed Oct. 5, 2010, which claims priority under PCT Article 8 to U.S. Application No. 61/264,069 filed Nov. 24, 2009 and U.S. Application No. 61/248,712 filed Oct. 5, 2009, each of which is incorporated herein by reference in its entirety.

REFERENCE TO GOVERNMENT GRANTS

Portions of the disclosure herein may have been supported in part by grants from the National Science Foundation/Small Business Innovative Research Grant No. 0419821 and the National Institutes of Health/Small Business Technology Transfer Research Grant No. 1 R41 HL080825-01. The United States Government may have certain rights in this application.

FIELD OF THE INVENTION

The invention relates generally to devices, systems, and methods for carrying out adsorption processes for separating and purifying fluid mixtures and, more particularly, to portable devices, systems, and methods for separation and purification processes employing advanced molecular sieve materials, especially for concentrating medical oxygen.

BACKGROUND OF THE INVENTION

The supply of therapeutic oxygen to patients in homes and other residential settings is an important and growing segment of the health care industry. Oxygen can be supplied to a patient by liquid or compressed oxygen with an appropriate vaporization or pressure regulation system and a gas delivery cannula. Alternatively, oxygen can be supplied by the generation of oxygen using a small onsite air separation device or medical oxygen concentrator located near the patient that delivers the generated oxygen via a cannula.

Respiratory oxygen usage rates typically range up to 3 LPM (liters per minute at 22° C. and 1 atmosphere pressure) for ambulatory patients with relatively low oxygen requirements, up to 5 LPM for patients with more serious respiratory problems and possibly limited mobility, and in certain cases up to 10 LPM for those with the most serious respiratory problems and more limited mobility. A patient initially may require a higher oxygen supply rate during an illness and later may require less oxygen as recovery is achieved. Alternatively, a patient may require increasing oxygen rates as a chronic condition worsens. A conserver may be used to provide oxygen flow only when the patient inhales, thereby reducing the amount of oxygen required by eliminating the supply of oxygen that is wasted when the patient exhales.

Portable medical oxygen concentrators often are preferred over liquid or compressed oxygen supply systems in home and residential settings, and small air separation devices for these applications are being developed by numerous vendors in the home health care field. Patients typically are encouraged to be ambulatory whenever possible to increase the effectiveness of oxygen therapy and improve their overall health. The portability of a medical oxygen concentrator therefore is an important feature allowing the patient to move about easily and comfortably. To maximize portability and ease of use, the medical oxygen concentrator must be designed to have minimum weight and compact dimensions. Patient ambulation time can be maximized by the use of a conserver.

There is a need in the home health care field for an improved, lightweight, battery-powered portable oxygen concentrator for delivering oxygen product to ambulatory patients. These patients typically require a concentrator that can generate up to about 3 LPM of oxygen on a continuous basis and that includes a built-in conserver that maximizes ambulation time. The invention is directed to these, as well as other, important ends.

SUMMARY OF THE INVENTION

The invention provides lightweight, portable oxygen concentrators that operate using an ultra rapid, sub one second, adsorption cycle based on advanced molecular sieve materials. The amount of sieve material utilized is a fraction of that used in conventional portable devices. This dramatically reduces the volume, weight, and cost of the device. Innovations in valve configuration, moisture control, case and battery design, and replaceable sieve module are described. Patients with breathing disorders and others requiring medical oxygen are provided with a long lasting, low cost alternative to existing portable oxygen supply devices.

In one embodiment, the invention is directed to removable modules for a portable oxygen concentrator, comprising:
at least one cartridge, comprising:
a housing having a feed end and a product end;
at least one input port for incoming air flow in said feed end;
a feed end plug;
a diffusion channel in said feed end;
an optional rupture plate for said input port;
at least one adsorbent bed contained in said housing, wherein said adsorbent bed comprises at least one molecular sieve material having an average particle size of about 60 vim to 180 µm and having a substantially spherical shape;
wherein said adsorbent bed has an aspect ratio of length to diameter of less than about 6;
an optional fibrous pad positioned at either end or both ends of said adsorbent bed;
at least one output port for an oxygen-enriched product flow in said product end; and
a product end plug comprising a gas flow controls and at least one collection channel;
at least one enriched-oxygen product tube, comprising:
an input end plug;
an oxygen input port in said input end plug;
an output end plug;
an oxygen output port in said output end plug; and
an optional rupture plate for said oxygen output port; and
a product end block comprising at least one passageway for transport of said oxygen-enriched product;
wherein said at least one cartridge and said at least one enriched-oxygen product tube are connected to said product end block.

In another embodiment, the invention is directed to manifolds for portable oxygen concentrators, comprising:
    a solid body having a passageway for transporting fluid;
    a connection for fresh air from a compressor to said passageway for transporting fluid;
    a 2-way compressor valve within said connection for fresh air;
    at least one first connection from said passageway to a cartridge comprising an adsorbent bed for separating air components;
    at least one second connection to said passageway from an oxygen-enriched product source;
    a valve within said second connection;
    two 3-way adsorbent bed valves within said passageway for transporting fluids positioned on both sides of said first connection;
    at least one exhaust port;
    an optional piercing mechanism attached to said solid body at said one first connection; and
    an optional piercing mechanism attached to said solid body at said one second connection.

In yet other embodiments, the invention is directed to portable oxygen concentrators, comprising:
    at least one removable module described herein;
    a compressor;
    an optional moisture control unit comprising a getter material for moisture positioned between said compressor and said inlet port of said removable module;
    a manifold to control gas flow into and out of said removable module comprising:
        a solid body having a passageway for transporting fluid;
        a connection for fresh air from a compressor to said passageway for transporting fluid;
        a 2-way compressor valve within said connection for fresh air;
        at least one first connection from said passageway to a cartridge comprising an adsorbent bed for separating air components;
        at least one second connection to said passageway from an oxygen-enriched product source;
        a valve within said second connection;
        two 3-way adsorbent bed valves within said passageway for transporting fluids positioned on both sides of said first connection;
        at least one exhaust port;
        an optional piercing mechanism attached to said solid body at said one first connection; and
        an optional piercing mechanism attached to said solid body at said one second connection;
    at least one optional moisture control unit;
    an optional oxygen sensor; and
    at least one battery cell.

In other embodiments, the invention is directed to systems, comprising:
    a portable oxygen concentrator described herein;
    a docking station; and
    a battery recharger.

In another embodiment, the invention is directed to methods of producing an oxygen-enriched gas flow, comprising:
    compressing an ambient air flow comprising oxygen and nitrogen to form a compressed air flow;
    transporting said compressed flow through an adsorbent bed to adsorb at least a portion of said nitrogen to form an oxygen-enriched gas flow; and
    removing said oxygen-enriched gas flow to form an oxygen-enriched product;
    wherein the pressure drop across said adsorbent bed is less than about 50 kPa.

The method may further comprise the step of desorbing from said adsorbent bed said portion of said nitrogen. The method may further comprise the step of exhausting said portion of said nitrogen desorbed from said adsorbent bed. The method may further comprise the step of collecting said oxygen-enriched product. The oxygen-enriched product is delivered to a recipient in need thereof.

In another embodiment, the invention is directed to methods of reducing the power requirement of a zirconium-based oxygen sensor, comprising:
    intermittently operating said zirconium-based oxygen sensor.

In another embodiment, the invention is directed to methods of reducing the power requirement of a zirconium-based oxygen sensor comprising a heater and a heater control, said method comprising:
    modulating the pulse-width of said heater control of said heater during operation of said zirconium-based oxygen sensor.

In another embodiment, the invention is directed to methods of increasing the lifetime of an electrochemical oxygen sensor in a portable oxygen concentrator, comprising:
    periodically turning gas flow off to said electrochemical oxygen sensor in said portable oxygen concentrator.

In another embodiment, the invention is directed to portable oxygen concentrator systems, comprising:
    a portable oxygen concentrator module having a first partial handle portion and at least one removable module having an enriched-oxygen product tube and at least one cartridge comprising adsorbent; and
    a battery pack module having a second partial handle portion;
    wherein said battery pack module releasably connects to said portable oxygen concentrator module;
    wherein said first partial handle portion and said second partial handle portion align to form a single integrated handle; and
    wherein said first partial handle portion inserts and secures said removable module in said portable oxygen concentrator system by lever action.

In another embodiment, the invention is directed to methods of reducing moisture content and increase throughput in a portable oxygen concentrator providing an enriched-oxygen product, comprising:
    providing a moisture control unit comprising a getter material that scavenges moisture when said portable oxygen concentrator is not operating;
    providing compressed air comprising oxygen and nitrogen to an adsorbent bed to adsorb said nitrogen and produce said enriched-oxygen product;
    wherein said getter material is gas impervious to prevent contamination of said enriched-oxygen product by said nitrogen in said compressed gas.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIG. 12A shows the individual adsorbent particle beads. FIG. 12B shows the small zeolite crystal component parts of the individual adsorbent particle beads.

Figure 1:
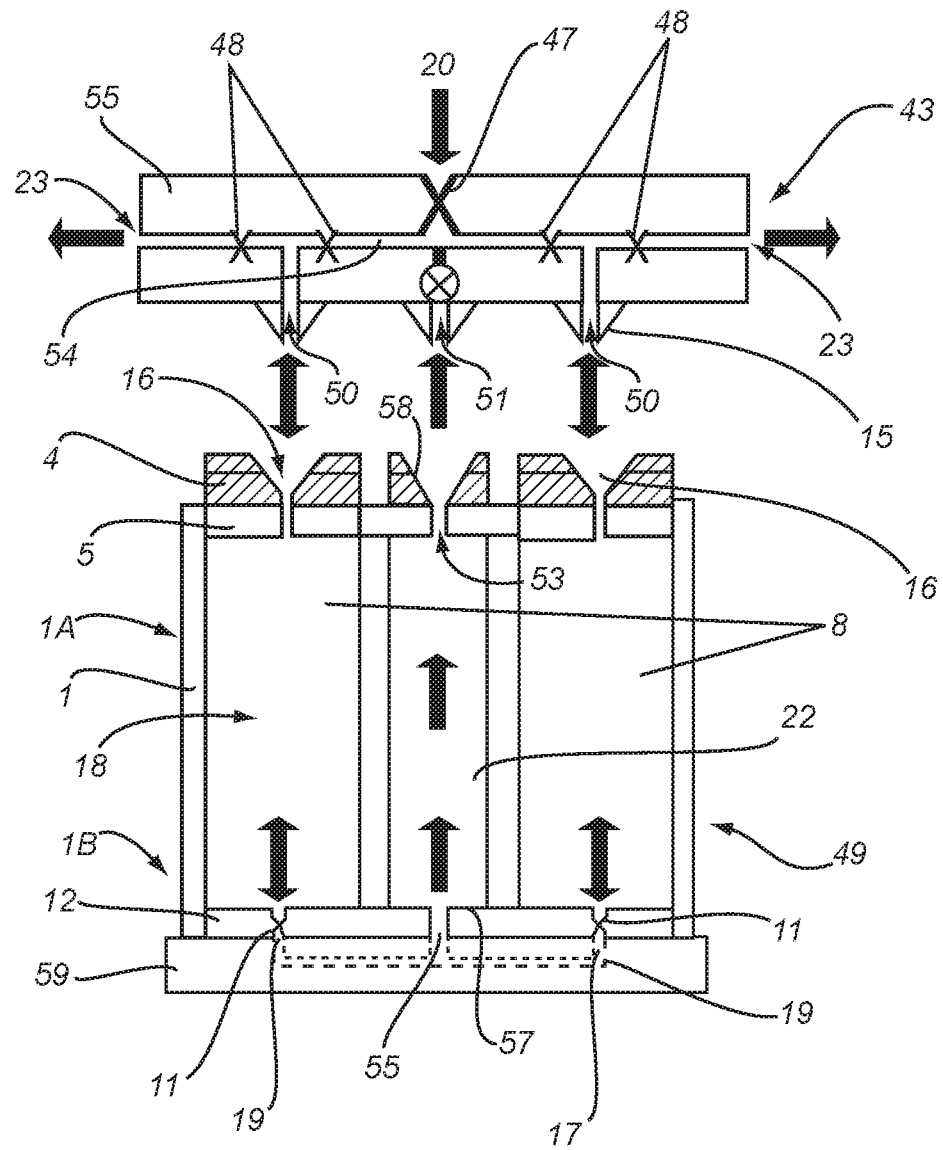
FIG. 1 is a cross-sectional view of the removable module 49 and the manifold 12 portions of a portable oxygen concentrator 43.

| Part Number | Description |
|---|---|
| 1 | Housing |
| 1A | Feed end of housing |
| 1B | Product end of housing |
| 2 | Compressor |
| 3 | Rupture plate |
| 4 | Feed end plug |
| 5 | Diffusion channel |
| 6 | Fibrous pad |
| 7 | Pre-weakened pattern |
| 8 | Adsorbent bed |
| 9 | Fibrous pad |
| 10 | Collection channel |
| 11 | Gas flow control orifice |
| 12 | Product end plug |
| 13 | Manifold |
| 14 | Seal |
| 15 | Piercing mechanism |
| 16 | Input port |
| 17 | Output port |
| 18 | Cartridge |
| 19 | Center feed hole |
| 20 | Passageway for compressed fresh air |
| 21 | Connection for an enriched oxygen product |
| 22 | Enriched oxygen product tube |
| 23 | Exhaust port |
| 24 | Moisture control unit |
| 25 | Oxygen sensor |
| 26 | Battery cell |
| 27 | Outer chamber |
| 28 | Inner chamber |
| 29 | Muffler |
| 30 | Cannula |
| 31 | Conserver |
| 32 | Docking station |
| 33 | Battery recharger |
| 34 | Battery cell |
| 35 | Battery pack case |
| 36 | Protection circuit module |
| 37 | Back plate |
| 38 | Battery pack handle |
| 39 | Portable oxygen concentrator handle |
| 40 | Battery pack module |
| 41 | Tabs |
| 42 | Recessed female connectors for positive and negative terminals |
| 43 | Portable oxygen concentrator module (without battery pack module) |
| 44 | Back pressure device |
| 45 | Entry port (FIG. 11) |
| 46 | Exit port (FIG. 11) |
| 47 | 2-way compressor valve |
| 48 | 3-way adsorbent bed valve |
| 49 | Removable module |
| 50 | Passageway to/from cartridge |
| 51 | Passageway from enriched-oxygen product tube 22 |
| 52 | Oxygen input port in enriched oxygen product tube 22 |
| 53 | Oxygen output port in enriched oxygen product tube 22 |
| 54 | Manifold passageway |
| 55 | Solid body |
| 56 | Valve |
| 57 | Input end plug in enriched-oxygen product tube 22 |
| 58 | Output end plug in enriched-oxygen product tube 22 |
| 59 | Product end block |
| 60 | Electronic controls |
| 61 | Inlet particulate air filter |

DETAILED DESCRIPTION OF THE INVENTION

The invention provides lightweight, portable oxygen concentrators that operate using an ultra rapid, sub one second, adsorption cycle based on advanced molecular sieve materials. The amount of sieve material utilized is a fraction of that used in conventional portable devices. This dramatically reduces the volume, weight, and cost of the device. Innovations in valve configuration, moisture control, case and battery design, and replaceable sieve module are described. Patients with breathing disorders and others requiring medical oxygen are provided with a long lasting, low cost alternative to existing portable oxygen supply devices.

Definitions

The following definitions are provided for the full understanding of terms used in this specification.

As used herein, the article "a" means "at least one", unless the context in which the article is used clearly indicates otherwise.

As used herein, the terms "separation" and "separating" mean the act or process of isolating or extracting from or of becoming isolated from a mixture (a composition of two or more substances that are not chemically combined).

As used herein, the terms "purification" and "purifying" means the act or process of separating and removing from anything that which is impure or noxious, or heterogeneous or foreign to it.

As used herein, the term "fluid" refers to a continuous amorphous substance that tends to flow and to conform to the outline of its container, including a liquid or a gas, and specifically includes solutions (where solids dissolved in the liquid or gas) and suspensions (where solids are suspended in liquid or gas).

As used herein, the term "portable" refers to a device that may be capable of being carried or moved. Preferably, the term refers to a device that may be carried by an adult or child with little or no effort. However, the term also refers to a device that is not permanently affixed to a permanent structure and is of sufficiently low mass and bulk that it may be easily transported as part of a vehicle or transportation device. Preferably, the portable oxygen concentrators of the invention weigh less than about 5 kg.

As used herein, the term "chamber" refers to a three-dimensional volume having an generally solid outer surface that is generally elliptical or circular in cross-sectional shape.

The term "adsorbent" or "adsorbent contactor" refers to an adsorbent or a membrane containing an adsorbent.

Reference will now be made in detail to the preferred embodiments of the invention, examples of which are illustrated in the drawings and the examples. This invention may, however, be embodied in many different forms and should not be construed as limited to the embodiments set forth herein. In addition and as will be appreciated by one of skill in the art, the invention may be embodied as a product, method, system or process.

In one embodiment, the invention is directed to removable modules for a portable oxygen concentrator, comprising:
at least one cartridge, comprising:
a housing having a feed end and a product end;
at least one input port for incoming air flow in said feed end;
a feed end plug;
a diffusion channel in said feed end;
an optional rupture plate for said input port;
at least one adsorbent bed contained in said housing, wherein said adsorbent bed comprises at least one molecular sieve material having an average particle size of about 60 μm to 180 μm and having a substantially spherical shape;
wherein said adsorbent bed has an aspect ratio of length to diameter of less than about 6;
an optional fibrous pad positioned at either end or both ends of said adsorbent bed;
at least one output port for an oxygen-enriched product flow in said product end; and
a product end plug comprising a gas flow controls and at least one collection channel;
at least one enriched-oxygen product tube, comprising:
an input end plug;
an oxygen input port in said input end plug;
an output end plug;
an oxygen output port in said output end plug; and
an optional rupture plate for said oxygen output port; and
a product end block comprising at least one passageway for transport of said oxygen-enriched product;
wherein said at least one cartridge and said at least enriched-oxygen product tube are connected to said product end block.

In another embodiment, the invention is directed to manifolds for a portable oxygen concentrator, comprising:
a solid body having a passageway for transporting fluid;
a connection for fresh air from a compressor to said passageway for transporting fluid;
a 2-way compressor valve within said connection for fresh air;
at least one first connection from said passageway to a cartridge comprising an adsorbent bed for separating air components;
at least one second connection to said passageway from an oxygen-enriched product source;
a valve within said second connection;
two 3-way adsorbent bed valves within said passageway for transporting fluids positioned on both sides of said first connection;
at least one exhaust port;
an optional piercing mechanism attached to said solid body at said one first connection; and
an optional piercing mechanism attached to said solid body at said one second connection.

In another embodiment, the invention is directed to portable oxygen concentrators, comprising:
at least one removable module of claim 1;
a compressor;
an optional moisture control unit comprising a getter material for moisture positioned between said compressor and said inlet port of said removable module;
a manifold to control gas flow into and out of said removable module comprising:
a solid body having a passageway for transporting fluid;
a connection for fresh air from a compressor to said passageway for transporting fluid;
a 2-way compressor valve within said connection for fresh air;
at least one first connection from said passageway to a cartridge comprising an adsorbent bed for separating air components;
at least one second connection to said passageway from an oxygen-enriched product source;
a valve within said second connection;
two 3-way adsorbent bed valves within said passageway for transporting fluids positioned on both sides of said first connection;
at least one exhaust port;
an optional piercing mechanism attached to said solid body at said one first connection; and
an optional piercing mechanism attached to said solid body at said one second connection;
at least one optional moisture control unit;

an optional oxygen sensor; and at least one battery cell.

To more fully understand the invention, the various embodiments will be described with respect to the figures.

Figure 18:
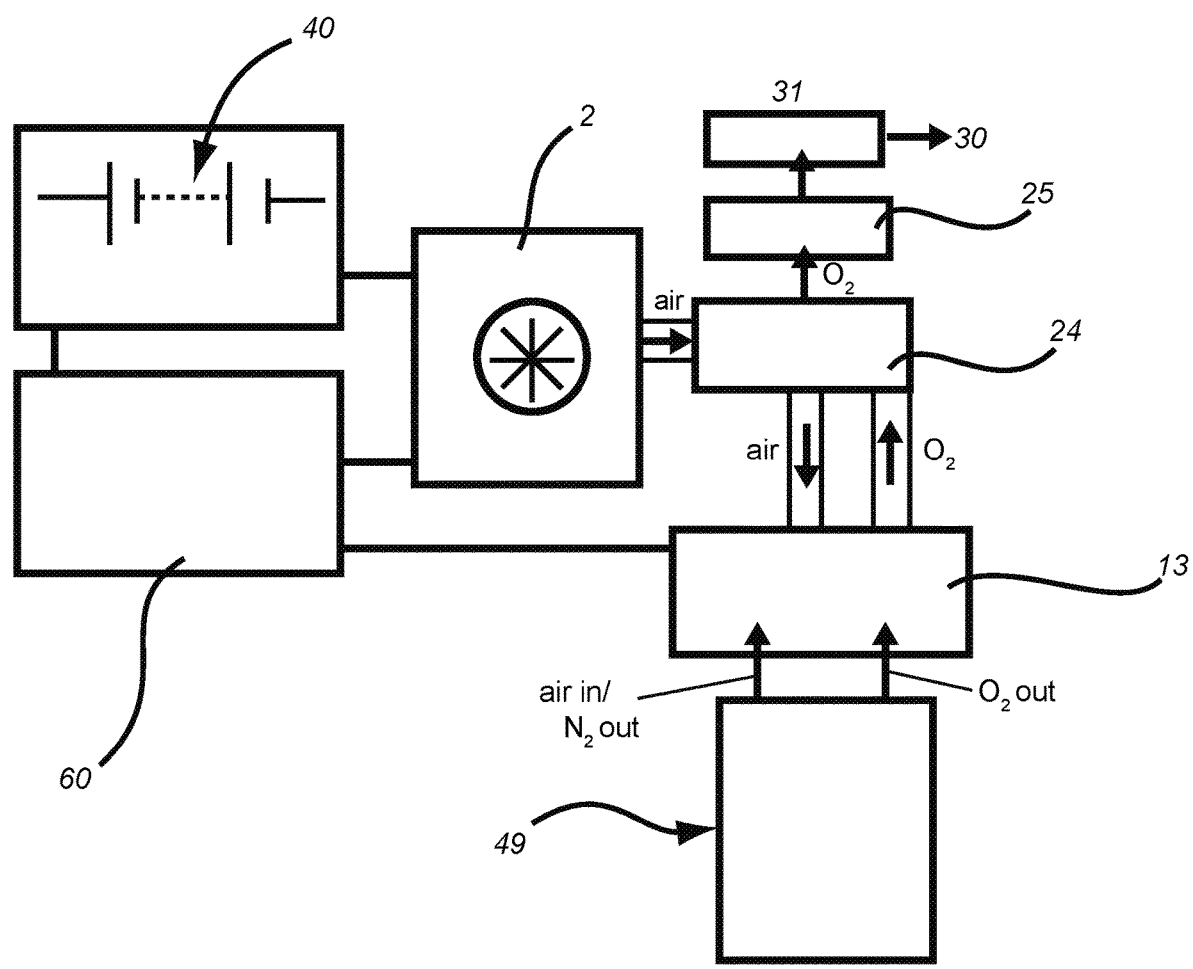
FIG. 18 is a block diagram of some of the components of an embodiment of the portable oxygen concentrator, including removable module 49, manifold 13, compressor 2, moisture control unit 24, oxygen sensor 25, conserver 31, cannula 30 (not shown), battery pack 40, and electronic controls 60.

FIG. 18 is a block diagram of some of the components of an embodiment of the portable oxygen concentrator, including the removable module 49, manifold 13, compressor 2, moisture control unit 24, oxygen sensor 25, conserver 31, cannula 30 (not shown), battery pack 40, and electronic controls 60.

FIG. 1 is a cross-sectional view of the removable module 49 and the manifold 12 portions of a portable oxygen concentrator 43 showing compressed air flow from a compressor 20 (not shown).

The removable module 49 in the embodiment of FIG. 1 has two cartridges 18. The cartridge 18 has a housing 1 having a feed end 1A and a product end 1B; at least one input port 16 for incoming air flow in said feed end 1A; a feed end plug 4; a diffusion channel 5 in said feed end 1A; an optional rupture plate 3 for said input port 16; and at least one adsorbent bed 8 contained in said housing 1, at least one output port 17 for an oxygen-enriched product flow in said product end 1B; and a product end plug 12 comprising a gas flow controls 11 and at least one collection channel 10. The adsorbent bed comprises at least one molecular sieve material having an average particle size of about 60 µm to 180 µm and having a substantially spherical shape. The adsorbent bed has an aspect ratio of length to diameter of less than about 6. Optional the cartridge has fibrous pad 6, 9 positioned at either end or both ends of said adsorbent bed.

The removable module 49 in the embodiment of FIG. 1 has at least one enriched-oxygen product tube 22, which has an input end plug 57; an oxygen input port 52 in said input end plug 57; an output end plug 58; an oxygen output port 53 in the output end plug 58; and an optional rupture plate 3 for the oxygen output port.

The removable module 49 in the embodiment of FIG. 1 has a product end block 59 has passageway 19 for transport of said oxygen-enriched product. Each cartridge 18 and the enriched-oxygen product tube 22 are connected to said product end block 59.

The portable oxygen concentrator in the embodiment of FIG. 1 also has a manifold 13 to control gas flow into and out of the removable module 18. The manifold has a solid body 55 having a passageway for transporting fluid 54. Within the solid body, there is also a connection for fresh air 20 from a compressor 2 to the passageway for transporting fluid 54 with a 2-way compressor valve 47 within the connection for fresh air 20, a first connection 50 from the passageway to a cartridge, a second connection 51 to the passageway from an oxygen-enriched product source. Also, there is a valve 56 within the second connection 51. Two 3-way adsorbent bed valves 48 are found within the passageway for transporting fluids and are positioned on both sides of said first connection 50. The passageway leads to an exhaust port 23. The manifold optionally has a piercing mechanism 15 attached to the solid body at the first connection and an optional piercing mechanism 15 attached to the solid body at the second connection.

Figure 1A:
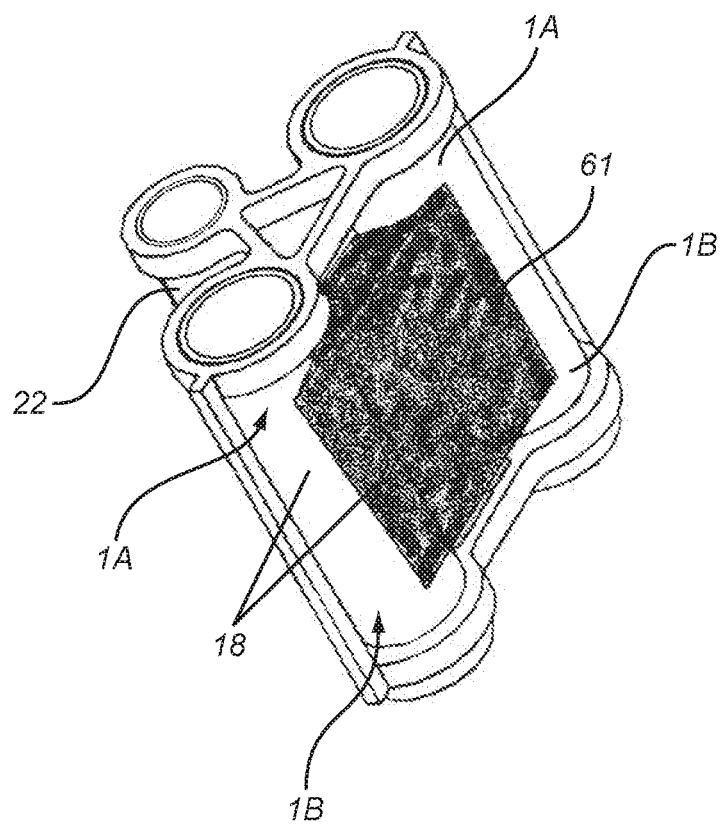
FIG. 1A is a schematic diagram of a removable module 49 having two cartridges 18, an enriched oxygen product tube 22, and inlet particulate air filter 61.

FIG. 1A is a schematic diagram of a removable module 49 having two cartridges 18, an enriched oxygen product tube 22, and inlet particulate air filter 61.

Figure 2:
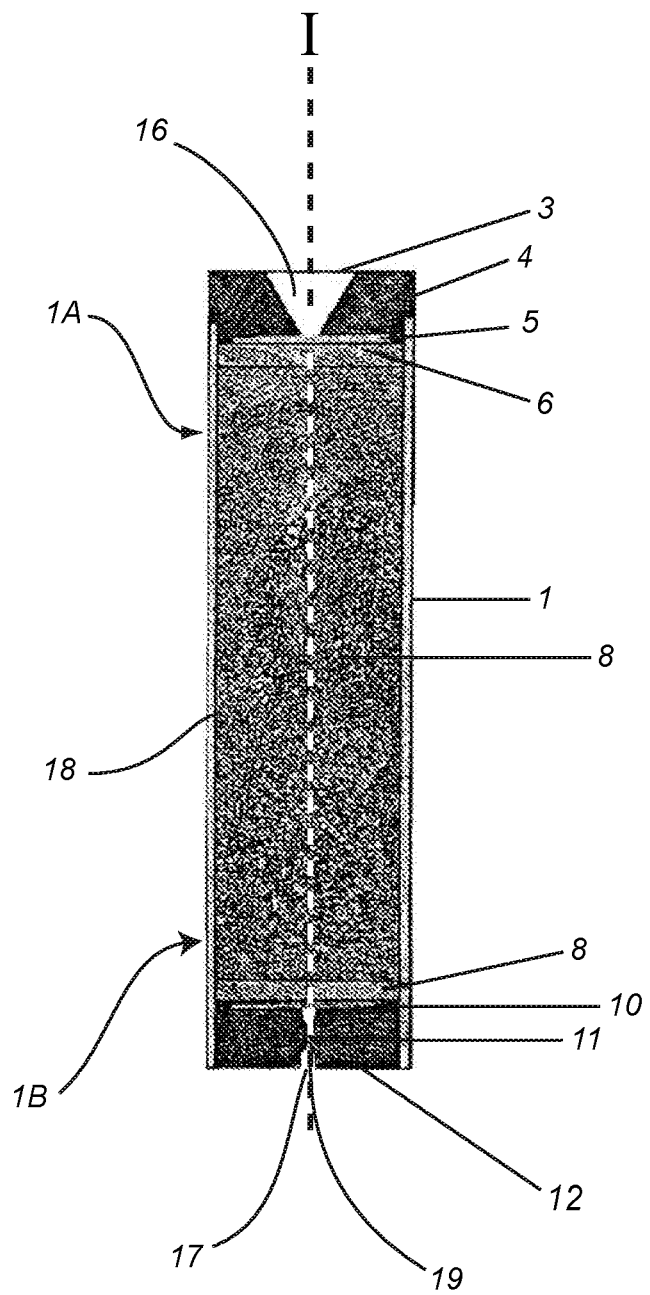
FIG. 2 is a vertical cross-section of the removable module 18 showing a rupture plate 3 covering the feed end plug 4 to seal the adsorbent bed 8 and prevent contamination, especially contamination from moisture, during storage prior to use.

FIG. 2 is a vertical cross-section of the cartridge 18 of the removable module 49 of one embodiment of the invention showing a rupture plate 3 covering the feed end plug 4 to seal the adsorbent bed 8 and prevent contamination, especially contamination from moisture, during storage prior to use. Housing 1 has a feed end 1A (which is also the exhaust end with respect to the nitrogen exhausted from the device) and a product end 1B (with respect to the oxygen-enriched product gas). In the feed end (i.e., where the compressed fresh air is received into removable module), there is at least one input port 16 for incoming air flow in said feed end, a feed end plug 4 (which can be made from such materials as polymers or lightweight metals), a diffusion channel 5, and an optional rupture plate 3 for said input port. In the product end (i.e., where one of the fluid flows in enriched in oxygen after passing through the adsorbent beds described herein), there is a product end plug 12 comprising a gas flow control orifice 11, at least one collection channel 10, and at least one passageway (center feed hole 19) for transport of said fluid product, and an optional rupture plate 3 for said output port 17. Housed within the removable module is at least one adsorbent bed 8 contained in said housing 1, wherein said adsorbent bed comprises at least one molecular sieve material having an average particle size of about 60 µm to 180 µm and having a substantially spherical shape. The adsorbent bed has an aspect ratio of length to diameter of less than about 6. Optionally, a fibrous pad 6, 9 may be positioned at either end of said adsorbent bed.

Figure 3:
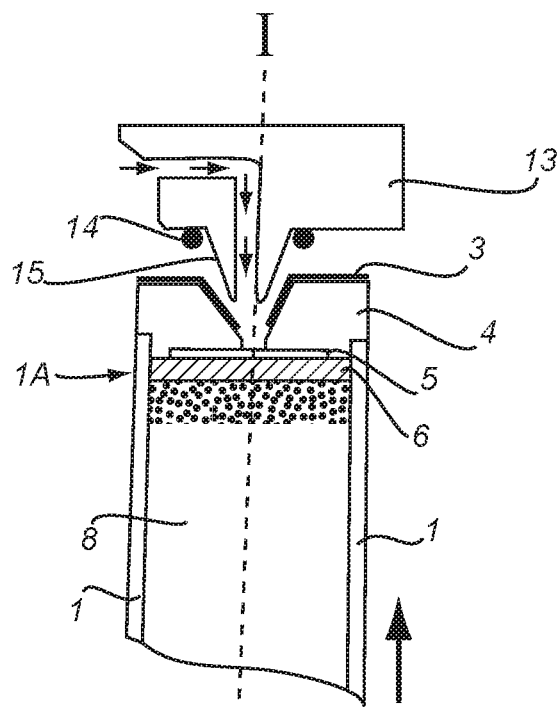
FIG. 3 is a vertical cross-section of the piercing mechanism 15 and module connections to the manifold 13 with the rupture plate 3 (shown after piercing by the piercing mechanism 15).

FIG. 3 is a vertical cross-section of the piercing mechanism 15 and module connections to the manifold 13 with the rupture plate 3 (shown after piercing by the piercing mechanism 15). As the removable module 18 is moved toward the piercing mechanism on the manifold 13, the rupture plate 3 is pierced thereby permitted compressed fresh air from the compressor 2 (not shown) to enter the feed end 1A of the removable module 18 through the feed end plug 4 into the diffusion channel 5 through the fibrous pad 6 and finally into the adsorbent bed 8. A seal 14, such as an O-ring or gasket, seals the connection.

Figure 3A:
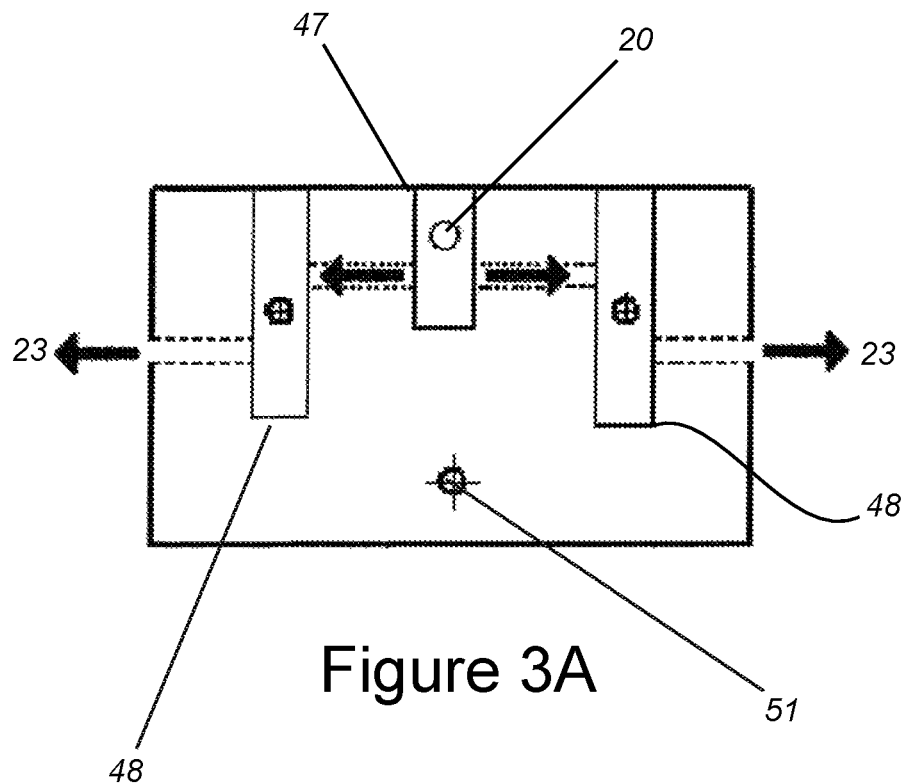
FIG. 3A is a vertical cross-section of the valving in the manifold 13 of one embodiment.
Figure 3B:
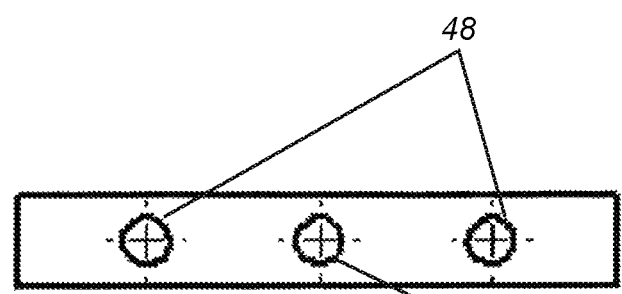
FIG. 3B is a top view of the valving in the manifold 13 of one embodiment.

FIG. 3A is a vertical cross-section of the valving in the manifold 13 in an embodiment having two cartridges 18 and a single enriched oxygen product tube 22. FIG. 3B is a top view of the valving in the manifold 13. In this embodiment, there are two 3-way valves 48 to control gas flow into and out of the adsorbent beds and single 2-way valve 47 to control the flow of compressed air from the compressor 2 (not shown) through the connection 20. In certain embodiments, the working components of the valves are integrated into the solid body 55 of the manifold 13 rather than mounted to it. The working components of the valves (i.e., the poppets, spools, or piezoelectric elements) are integrated into the solid body 55 to make it a more compact, lighter unit and the gas flow pathways 50, 51, and 54 are also contained within the manifold as in other arrangements where the valves are mounted onto the manifold. In certain embodiments, solenoids (not shown) actuate the valves and may either be contained within solid body 55 or may be mounted to it.

Figure 4:
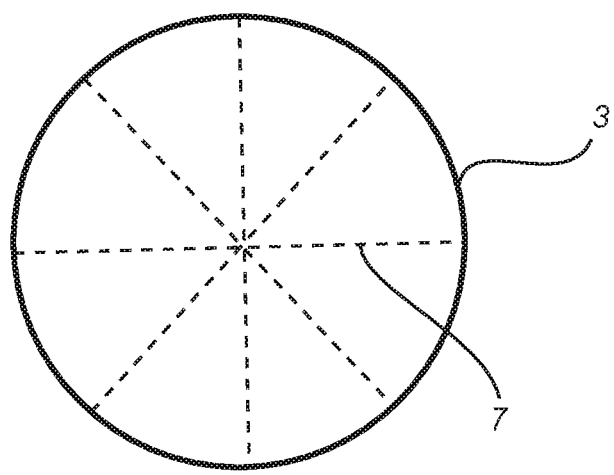
FIG. 4 is a plan view of the rupture plate 3 showing a pre-weakened pattern 7, which permits easy opening with the piercing mechanism 15 (not shown).

FIG. 4 is a plan view of the rupture plate 3 showing a pre-weakened pattern 7, which permits easy opening with the piercing mechanism 15 (not shown).

Figure 5:
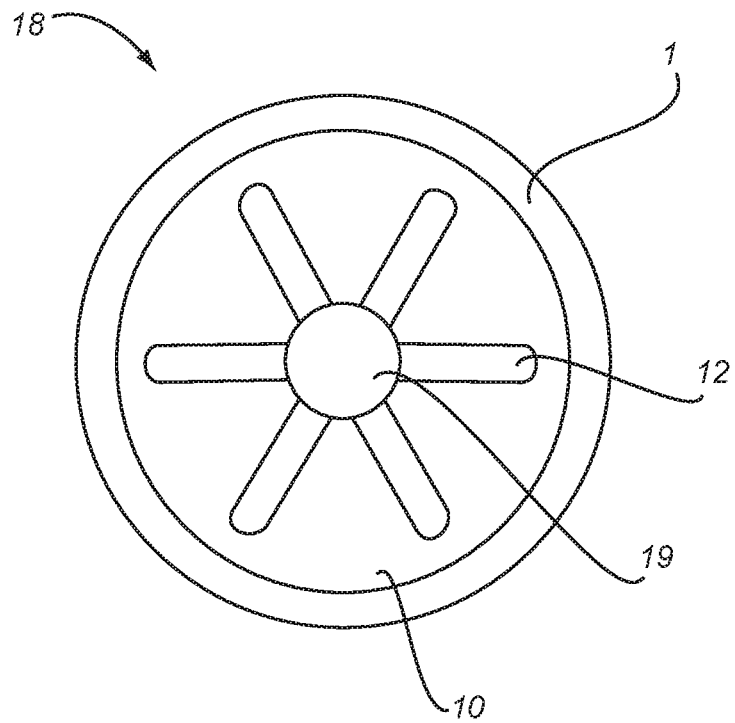
FIG. 5 is a plan view of the removable module 18 showing product end plug 12, center feed hole 19, and collection channel 10.

FIG. 5 is a plan view of the removable module 18 showing product end plug 12, center feed hole 19, and collection channel 10.

The portable oxygen concentrators (POC) of the various embodiments are designed to operate using ultra rapid cycle pressure swing adsorption where the cycles are less than one second in duration. Traditional POCs operate using cycles that are several seconds long. Pressure swing adsorption systems typically use adsorbent beds filled with spherical particles of the molecular sieve materials, especially zeolites, which preferentially adsorb nitrogen when they are filled with pressurized air, thus producing an oxygen-enriched product. When the beds are depressurized, the nitrogen is desorbed. Since the adsorption capacity for nitrogen of the beds is limited, shortening the cycle is advantageous in that it allows more output to be produced from a smaller quantity of adsorbent. Typical POCs use adsorbent beds that contain approximately 0.5 kilograms of adsorbent. The ultra rapid cycle operation of the devices of the various embodiments allows the use of adsorbent beds that contain less than about 50 grams of adsorbent. This drastic reduction in the amount of adsorbent material required allows for a significant savings in mass and volume of the portable oxygen concentrator.

To operate using cycles of less than one second duration, advanced molecular sieve materials are required. Smaller particles are utilized to allow for more rapid diffusion of gas through the porous structure of the particle. The molecular sieve particles used in the invention range in diameter from about 60 µm to about 180 µm, and the preferred diameter range is between about 80 µm and about 120 µm. Conventional technology uses particles that range in size from about 0.4 mm to about 0.8 mm. The smaller size of the adsorbents employed in the various embodiments allows gases to diffuse in and out of the beads very rapidly so cycle times of 0.15 seconds are possible. This is at least ten (10) times faster than any cycle time used in any commercial separations device. Fast cycle times equate to smaller amounts of adsorbent being required to process the same amount of gas.

The relationship between cycle rate and adsorbent quantity required is roughly an inverse relationship, i.e., doubling cycle rate from 1 cycle per second to 2 cycles per second means that the typical separations system would go from using 0.5 kg of adsorbent to using 0.25 kg adsorbent. Conventional portable oxygen concentrators typically use about 300 grams to about 450 grams of adsorbent in a system that produces about 750 ml to about 1000 ml per minute of oxygen. The portable oxygen concentrator of the invention can use as little as about 5 grams to about 30 grams to produce the same amount of oxygen per minute. The considerable weight and volume reduction may be used to decrease the device size and weight, or to increase the size and volume of the battery, thereby providing longer operating time.

Figures 12A, 12B:
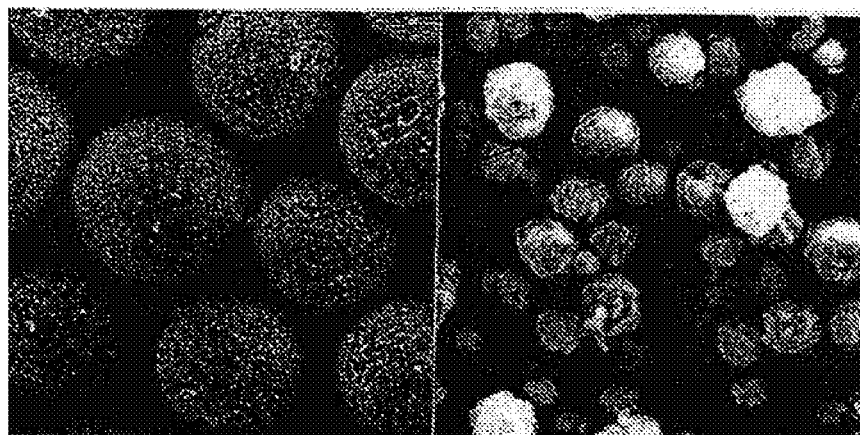
FIGS. 12A and 12B are scanning electron micrographs images detailing the regular, spherical nature of the adsorbents employed in the invention.

The particles must also be highly spherical, because any irregularity in their shape greatly increases the pressure drop through the adsorbent bed. FIGS. 12A and 12B are scanning electron micrographs images detailing the regular, spherical nature of the adsorbents employed in the invention. FIG. 12A shows the individual adsorbent particle beads. FIG. 12B shows the small zeolite crystal component parts of the individual adsorbent particle beads.

Most currently available molecular sieve materials for air separation have a lower limit diameter of about 560 micrometers. This diameter limits how fast gases can diffuse into and out of the adsorbent bead. This is why the fastest cycle time for commercially available oxygen concentrators is about 4 seconds. Most researchers believed that making the beads smaller would increase tortuosity to the point that an energy wasting pressure drop would be introduced. The present research showed that this was the case with irregular shaped adsorbents, but highly spherical beads, as small as 100 micrometers in diameter did not introduce too large a pressure drop as long as a certain sieve bed length to cycle rate ratio was maintained. This ratio is about 10 cm bed length to one second of cycle time. For example, a 0.5 second cycle time would require a 5 cm bed length. If, for a given cycle rate, a lager throughput is required, the sieve beds may be paralleled. For example, a pressure swing adsorption system having two beds that operate in alternating fashion, having dimensions of 7 cm long by 2 cm in diameter, can produce about 750 ml per minute of 94% purity oxygen at a cycle time of 0.7 seconds. If a production rate of 1500 ml per minute is required, the same cycle rate may be used by paralleling with two additional sieve beds having parallel inlet and outlet ports. Thus an oxygen concentrator having any desired output can be manufactured.

For practical reasons, there may be a minimum bed size and maximum cycle rate for a given application. Having more sieve material equates to less frequent sieve bed exchanges. It has been discovered that two 7 cm long by 2 cm diameter adsorbent beds strike the best balance between device size reduction and frequency of sieve bed replacement.

The molecular sieve material used in the module and portable oxygen concentrator of the invention imposes limitations upon the dimensions of the adsorbent bed. Beds longer than about 12 centimeters in length and about 2.5 centimeters in diameter are impractical due to excessive pressure drop through the bed. The preferred bed size is about 1.7 to about 2 cm in diameter, and about 7 cm to about 8 cm in length. The preferred ratio of the bed length to bed diameter is about 4.3:1. Each adsorbent bed is capable of producing a maximum of between 350 and 500 milliliters per minute of oxygen-enriched product of at least 85% purity. The beds are preferably used in pairs, and if more output is desired, multiple beds or sets of beds may be used.

Molecular sieve materials, such as zeolites, which are useful as adsorbents, are highly susceptible to contamination by water, and because of this and other factors such as particle attrition, the performance of oxygen concentrators degrades over time. Once a concentrator's performance has dropped to the extent that it is no longer able to provide adequate oxygen output (typically at least the equivalent of 2 liters per minute of 85% oxygen), the concentrator is generally replaced or the adsorbent is replaced by the manufacturer or a reseller. The life of the adsorbent is often the limiting factor in the life of the device. It is therefore advantageous to have an adsorbent that is replaceable by the user. The invention features a removable and replaceable adsorbent module that is designed to be patient friendly and require very little physical strength or dexterity to install. In certain embodiments, the module features two or more adsorbent beds, inlet ports for air that lead to each of the beds, an outlet port for the oxygen enriched product, and a product-end block that contains gas flow controls and passageways.

In a pressure swing adsorption system, the majority of the product gas is allowed to exit the system as output, and some of it is allowed to flow into the product end of the bed that is in its desorption stage in order to drive the desorbed nitrogen out of the bed and flood it with oxygen-enriched gas. Conventional oxygen concentrators achieve this by using a check valve to control the flow out of the bed, and an orifice to allow purge flow back into the bed. The invention simplifies this arrangement by using only an orifice whose diameter is selected to create sufficient pressure in the beds, control the output flow, and allow adequate purge flow. It is possible that this orifice preferentially allows free flow in one direction, while restricting it to a certain degree in the other direction. The orifices may be contained in the product-end block 59 of the module, as may passages to allow air to flow between the adsorbent beds and to the oxygen output port 17.

The module must be sealed to prevent moisture and other contaminants from entering the adsorbent during storage and installation. The ports are covered with rupture plates that are constructed of a material that is easily pierced, such as a plastic film or an aluminum foil. In preferred embodiments, the rupture plates are adhered to the top of the molecular sieve bed. The rupture plates are preferable pre-weakened (by die-stamping, laser ablation, or some other suitable method) to ensure that they rupture in a predictable pattern.

Figure 8:
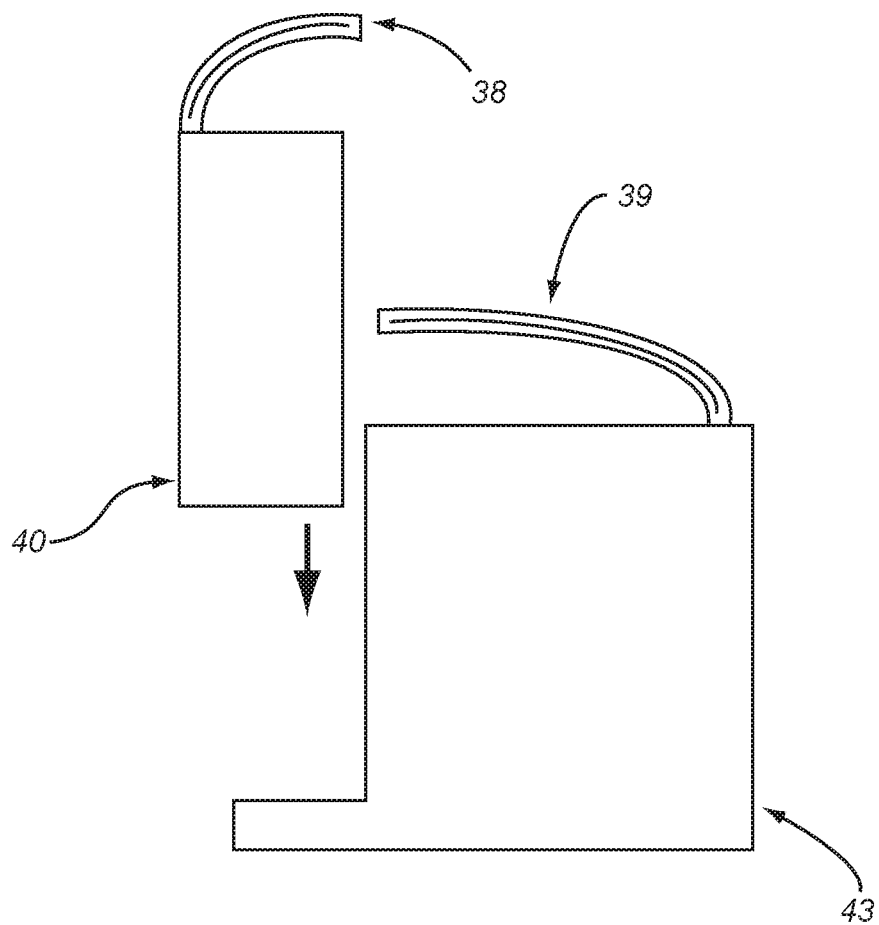
FIG. 8 is a side view of a portable oxygen concentrator system having a battery pack module and portable oxygen concentrator module.

When the module is installed into the oxygen concentrator, it connects to a manifold that controls the flow of gas in and out of the module. In certain embodiments, the manifold has a piercing mechanism that punctures the rupture plates as the module is installed. The piercing mechanism includes projections that are designed to pierce the rupture plates and push the rupture plate material aside so that it does not obstruct flow in/out of the module. In preferred embodiments, the module has sockets into which the piercing mechanism fits that are designed to minimize head space (dead volume). In certain embodiments, the interface between the module and the manifold is sealed with a flexible seal such as an o-ring or rubber gasket. After the module is in place, installation is completed by closing a mechanism that applies pressure to the module and holds it tight against the seal to ensure an airtight fit. In certain embodiments, the mechanism has a hinged "door" that closes against the module and a latch to hold the "door" closed. This door may also comprise the handle of the device, as shown in FIG. 8.

The gas flow manifold of the oxygen concentrator includes a connection for fresh air from the compressor, a connection for the oxygen tube which leads to the oxygen reservoir, and exhaust ports, which are connected to an optional muffler. In certain embodiments, a 3-way solenoid valve is mounted in or on the manifold to control the flow into and out of each of the adsorbent beds in the module. In certain embodiments, a 2-way valve is used to control the flow of pressure air from the compressor.

In certain embodiments having two cartridges with adsorbent beds, the operating cycle of the valves is as follows:
(1) The compressor valve opens, as does the 3-way valve connected to the first adsorbent bed, and the bed is pressurized.
(2) The compressor valve closes, and the 3-way valve connected to the second adsorbent bed opens while the first adsorbent bed valve remains open. This step allows pressurized, oxygen-enriched gas from the first bed to partially pressurize the second bed. This step is preferred because it decreases the amount of compressed air needed, thereby increasing the energy efficiency of the device.
(3) The 3-way valve connected to the first bed closes, and the first bed 1 enters its exhaust/desorption phase. The compressor valve opens, and the second bed is fully pressurized.
(4) Pressure from the second bed is used to partially pressurize the first bed (this step is the reverse of step 2).
The cycle then repeats.

The adsorbent/filter module includes a novel design that eliminates the springs commonly used to keep the bed packed tightly. With reference to FIG. 1, a housing 1, preferably in the form of a round tube constructed of aluminum, plastic, or other lightweight material, contains the bed of adsorbent material. A compliant, fibrous pad 6, 9 is placed at either end of the bed. The pad serves at least three purposes:

(1) to act as a filter and prevent microscopic dust particles created by attrition of the adsorbent material from escaping the bed;
(2) to act as a cushion to protect the adsorbent particles; and
(3) to restrain the bed.

The pads 6, 9 are held in place by plugs 4, 12 that are an interference fit with the housing. The feed end plug 4 contains the socket into which the piercing mechanism 15 fits (as shown in FIG. 3), and the product end plug 12 contains the air outlet and in one possible embodiment the flow control orifice 11. The surfaces of the plugs that contact the pads may have passageways cut in them to promote diffusion of gas across the surface of the bed, or alternatively, a diffusion plate may be inserted between the plugs and the pads. The assembly is pressed together using a mechanical press to ensure that the plugs are seated firmly against the pads and the adsorbent beds, effectively locking the adsorbent particles in place. Eliminating any movement of the adsorbent particles in this fashion greatly reduces attrition.

Absorbent Beds

The absorbent beds comprise at least one molecular sieve material having an average particle size of about 60 µm to 180 µm and having a substantially spherical shape. Preferred molecular sieve materials are aluminophosphate and silicoaluminophosphate (zeolite) types, and metal substituted aluminophosphate and silicoaluminophosphate (zeolite) molecular sieves (including, but not limited to, $Li^+$, $Na^+$, $K^+$, $Ca^{2+}$, $Ag^{1+}$ and/or $Mg^{2+}$-substituted aluminophoshpate and silicoaluminophosphate molecule sieves), especially as part of a polymer matrix. Such zeolite adsorbents are available from Arkema Inc., Philadelphia, Pa., USA.

The sorbent structure may further comprise at least one support. In certain embodiments, at least a portion of the sorbent is adhered to or embedded in the support. Preferably, the support is a series of micro-channels, laminar, a porous electrode; a series of concentric layers, or a combination thereof.

Suitable supports for use in the methods, devices, and systems of the invention include, but are not limited to, natural clay, calcined clay, modified clay, chemically treated clay, chemically modified clay, smectite clay, kaolin clay, sub-bentonite clay, kaolin-halloysite clay, kaolin-kaolonite clay, kaolin-nacrite clay, kaolin-anauxite clay, binary matrix material, tertiary matrix material, silica-thoria, silica-alumina, silica-alumina-thoria, silica-alumina-zirconia, fibrous material, colloidal silica material, colloidal alumina material, colloidal zirconia material, colloidal mixture, surface modified amorphous silicon dioxide nanoparticles, hydrated magnesium aluminum silicate, thermoplastic polymer, thermosetting polymer, ferrous support, non-ferrous support, electrically-conductive support, dielectric support, electromagnetic receptor, or a combination thereof. The support may be applied by sintering, pyrolysis, slurrying, vapor deposition, casting, electro-spraying, electrophoretic deposition, extrusion, laser deposition, electron beam deposition, silk screening, photo-lithography deposition, electrostatic self-assembly, high aspect ratio micromachining, LIGA-formation, atomic layer deposition, casting, stamping, or a combination thereof.

In certain preferred embodiments, each unit comprising sorbent structure may utilize different sorbents, wherein each of the sorbents is selective for a different component of the same or different mixture.

In certain embodiments, a combination of different molecular sieve material may be employed.

Moisture Management

The use of very small amounts of adsorbent has weight advantages but also creates challenges. All nitrogen selective adsorbents can be rendered non-functional if contaminated with moisture. Larger systems have sufficient quantities of adsorbent that moisture contamination is not a problem over the 3-year average device lifetime. Smaller devices may require periodic replacement of the adsorbent material. Because such a small quantity of adsorbent is used in the embodiments of the portable oxygen concentrator, moisture management becomes a significant issue. Two approaches may be employed to mitigate these problems in the various embodiments.

One approach is the use, for example, of an alumina or other adsorbent barrier between the compressed inlet air and the ultra-dry oxygen enriched gas (product). Moisture diffuses toward the oxygen side because of pressure differentials and $H_2O$ partial pressure differentials (equilibrium driven). Also, a second barrier between the compressed inlet gas (air) and the nitrogen enriched waste gas may be used. The moisture is driven toward the nitrogen waste gas side via a pressure differential mechanism. The barrier material (unlike a membrane) is not gas permeable.

In one embodiment, co-axial containers 24 are configured with the outer chamber 27 made of a lightweight metal, such as aluminum (27 in FIG. 11), and the inner chamber (28 in FIG. 11) comprising a water permeable material, described below.

In operation, feed air (directly from the compressor outlet) enters the outer chamber 27 on container 24, labeled A, and exits to a second container 24 of similar design, labeled B. Dry product oxygen from the adsorbent bed(s) 8 is directed into the inner chamber of A 28 and exits to the conserver 31 and/or a backpressure device 44. Waste nitrogen from the adsorbent bed 8 is directed through the inner chamber 28 of B and exits to an exhaust outlet 23 (not shown). Throughout operation of the device, a pressure differential exists across the water permeable material as well as a difference in relative humidity between the two gas streams. These differentials drive moisture from the more humid, higher pressure cylinder through the water permeable material and into the dry, lower pressure, inner chamber. This behavior is highly ideal. Moisture that inhibits oxygen separation capacity of the adsorbent is effectively removed prior to entering the sieve bed, thereby maximizing lifetime of the adsorbents. Furthermore, re-hydration of the dry oxygen is necessary before output to the patient thereby preventing patient discomfort due to ultra dry oxygen.

The prior art devices employ a variety of techniques to achieve moisture removal. These techniques include desiccant dryers, membrane filters, centrifugal devices, and the like. The moisture management system described herein is superior to the prior art techniques. The device of the invention is lightweight, low cost, and self-sustaining (i.e., does not need to be replaced during the lifetime of the concentrator). Furthermore, unlike membrane filters, the water-permeable material is impervious to nitrogen and oxygen, thus no undesirable nitrogen may enter the product stream. The water-permeable barrier comprises a material that shows high selectivity for moisture yet is not permeable to gases. This material may contain a hydroscopic adsorbent material, such as aluminum oxide, silica gel, and the like and combinations thereof, and may or may not include a binder. The material may be an extrudate, a casting, a sintered material, or an otherwise formed structure. Furthermore, the material may be incorporated within the walls of a barrier that is non-permeable to air or sealed within the walls of an existing barrier constructed from a material that is non-permeable to air. A functional grading of deliberate design within the walls of the adsorbent material may also be incorporated to further ensure non-permeation of gases.

The water-permeable barrier is highly unique in that it also serves as a "getter" material, or moisture sink, that acts to attract moisture from the product end, the sieve bed valves, and the valve manifold and any dry interconnections. Upon shutdown, the getter material sequesters any moisture remaining in or entering the system.

The moisture management system also serves as a pulse control system and acts as an oxygen reservoir.

In certain embodiments, the use of aluminum as the outer cylinder 27 promotes heat dissipation thereby maintaining maximum adsorption capacity in the sieve bed and aiding in the condensation and attraction of moisture in the feed stream to the water-permeable material.

The outer chamber material is impermeable to both water and gases. The inner chamber material is impermeable to gases yet highly permeable to water.

Figure 11:
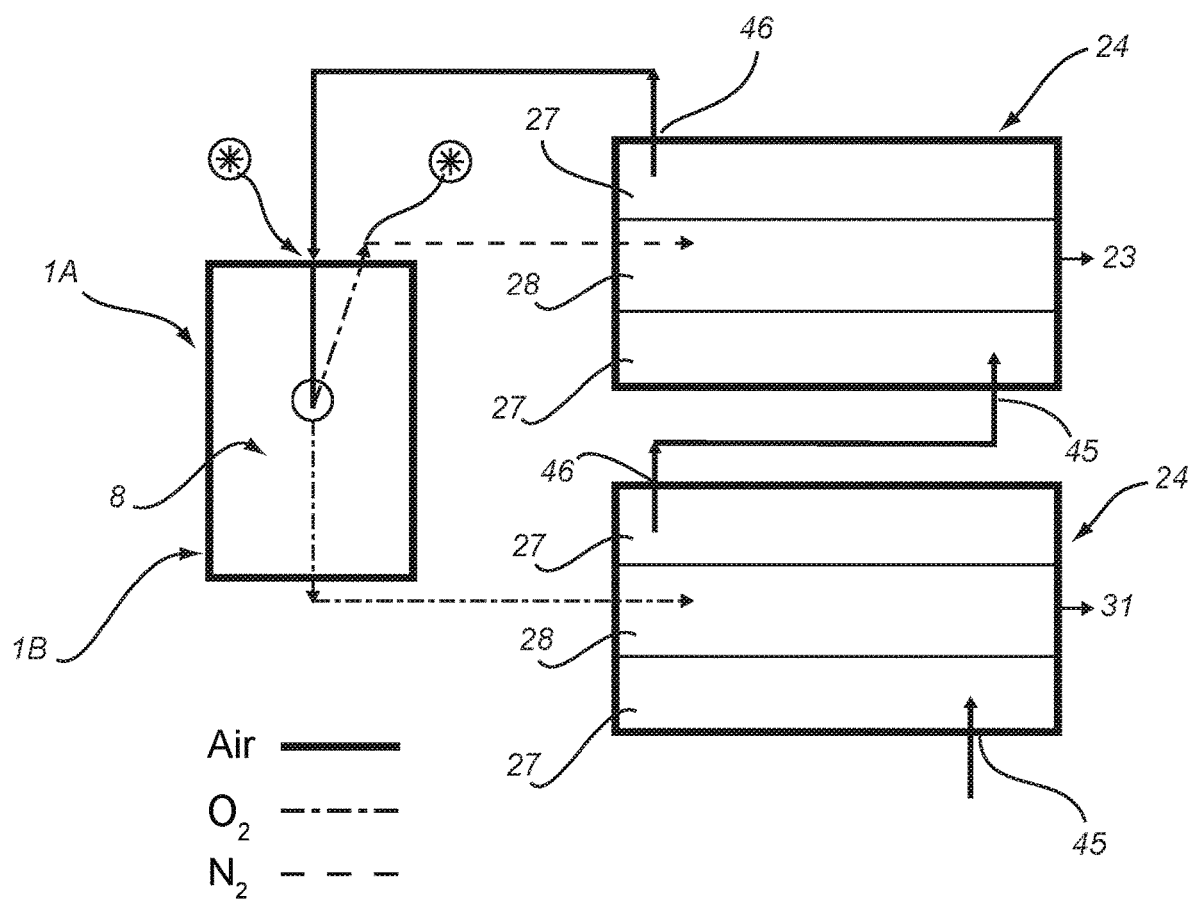
FIG. 11 is a schematic view of the moisture control unit of the portable oxygen concentrator.

Configuration of the moisture management system within the device has been described with a multiple container arrangement as depicted in FIG. 11 to have a greater impact upon moisture removal, however the device could similarly function with a single container.

Pressure swing adsorption (PSA) devices using zeolites have been used for many different separation applications of gases or liquids including the separation of air to produce medical grade oxygen. Many of these systems use hundreds or thousands of grams of zeolites depending on the application. Hundreds of grams of zeolites are used in two-zeolite-containing-column-separation systems designed to produce oxygen for long-term home applications. Moisture in the compressed air entering these air-separation systems is not typically a problem since one column is being used for air separation while the other is being regenerated and the cycle time between the columns is on the order of minutes.

The portable rapid cycle pressure swing air separation devices of the invention produce medical grade oxygen with a cycle time of approximately one-second between the advanced molecular sieve-containing beds. The unit is specifically designed as a light-weight portable system and uses only about 10 to 20 grams of a zeolite specifically designed for use in this rapid cycle system. Since small quantities of advanced molecular sieve materials (especially zeolites) are used in this system, precautions are utilized to both minimize the amount of moisture permitted to enter the zeolite columns and to protect the molecular sieve material from moisture entering the system from the air entrance port or through the oxygen exit port when the system is not in use.

A method for the simultaneous drying and humidifying of two separate gas streams in a PSA oxygen concentrator is described. Incoming feed air directed into a chamber containing, for example, coaxial tubes, the inner being comprised of a non-porous material with propensities towards water adsorption, surrenders moisture which then migrates through the adsorbent to the outgoing dry gas. Furthermore, the method allows for a moisture sink during periods of non-operation. The prior art contains many references to moisture removal. These techniques include desiccant dryers, membrane filters, centrifugal devices, etc. The moisture management system described is superior to past techniques. It is lightweight, low cost, and self-sustaining (does not need to be replaced during the lifetime of the concentrator). Furthermore, unlike membrane filters, the water-permeable material is impervious to nitrogen and oxygen, thus no undesirable nitrogen may enter the product stream.

In certain embodiments, the process used to minimize the moisture entering the portable oxygen concentrator utilizes a drying/re-moisturizing component located after the air compressor and prior to the adsorbent beds. The drying/re-moisturizing apparatus contains two co-axial container systems (two moisture control unit components 24 shown in FIG. 11 as (A) and (B), for example, as a co-axial tubular design). The containers 24 are sealed near the ends producing an outer chamber 27 and an inner chamber 28. Each container has an entry port 45 and exit port 46. The outer container wall is non-permeable to air or moisture with the entry port located near one end of the container and connected to the compressor 2 (not shown in FIG. 11). The outer chamber wall is fabricated from a lightweight metal, such as aluminum, which also serves to dissipate heat of compression and enhance condensation of moisture within the chamber for both co-axial systems A and B. The moist compressed air is introduced through the entry port of the first co-axial container system (A), passes through the outer container chamber 27, and leaves through the exit port 46 of the outer chamber. During this passage, moisture is removed from the air stream as discussed below. The compressed air then flows through the outer container of an identical co-axial container system (B) where the moisture content is further reduced and the air then enters the zeolite compartment (C) where it is separated into an oxygen stream and a nitrogen stream.

Function of the moisture permeable membrane is enhanced by two features of operation: a pressure and moisture differential across the material.

An additional barrier to protect against incoming moisture may be incorporated directly into the sieve bed in the form of a guard layer. The guard layer may contain adsorbents with high propensities for moisture uptake similar to those used to form the inner wall of the moisture uptake chambers. The adsorbents may be chemically or physically sequestered within fibrous forms to prohibit a mixing with those adsorbents responsible for oxygen separation.

The walls of the inner chamber 28 of co-axial systems (A) and (B) comprise a getter material, which is non-permeable to air but permeable to moisture and preferably comprises an adsorbent fabricated within the walls of the container. The adsorbent located in the walls of the inner chamber 28 (a "getter" for moisture) can be (1) incorporated within the walls of a container that is non-permeable to air, (2) sealed within the walls of an existing container constructed from a material that is non-permeable to air, and/or (3) a container produced from an extruded adsorbent permeable to moisture but non-permeable to air. The adsorbent may be aluminum oxide, silica gel, or others obvious to those trained in the art. The extruded inner container walls may be of tubular shape or other designs, for example, a star-shaped tube or other designs that maximize the surface area exposed to the moist compressed air. As moist air passes through the outer container it contacts the wall of the inner container. The adsorbent in the inner container wall sequesters moisture from the compressed air. Two factors enhance moisture transfer from the outer container to the inner container in co-axial systems (A) and (B). The first is that the compressed air pressure in the outer chamber 27 is much higher than the pressure in the inner chamber 28. The second is that the oxygen product stream passing through the inner container of co-axial system (A) is dry and is readily re-moisturized and the moisture is carried away with the product stream. The nitrogen stream leaving sieve bed (C) and passing through the inner container of co-axial system (B) has a lower moisture content than the compressed air passing through the outer container of (B) and moisture is carried away with the nitrogen produced. Both of these factors enhance moisture removal from the compressed air and provide a re-moisturized oxygen product for inhalation thereby preventing patient discomfort due to ultra-dry oxygen.

Adsorbents are preferably utilized in the moisture control unit 24. However, membranes may be used for the drying apparatus such as the one described above. However, the membranes can permit passage of some nitrogen through the membrane and dilute the medical grade oxygen product passing through the inner container of co-axial system (A). The moisture control unit may contain bacteria-suppressing materials, such as colloidal silver.

The second co-axial container system (B) not only further reduces the moisture content of the compressed air but also serves as a "moisture getter" for moisture that may enter the portable rapid cycle pressure swing air separation system when it is not in use. By using a co-axial drying system on the advanced molecular sieve bed inlet and outlets, upon shutdown, the device sequesters moisture from any air entering the device through the air stream entrance or from moisture entering the device through the oxygen and nitrogen exit ports.

The second moisture management approach is to make the sieve beds easily replaceable by the user. V-Box Inc. has a belt wearable concentrator that has separate pouches for compressor, sieve beds, and batteries. This makes the sieve beds replaceable, but only as a separate unit and it requires making 8 pneumatic connections, each with a length of tubing that introduces sizeable flow restrictions. As described herein, in one embodiment, sieve bed architecture has been developed that has only three pneumatic connection points, is very simple to replace, and is hermetically sealed until it is inserted into the oxygen concentrator. Rupture plates preferably cover the ports. These plates are pierced automatically when the sieve module is inserted into the concentrator body. A moisture control unit may be attached to the sieve module so that both the adsorbent bed and filter are changed at the same time. In very moist environments, the adsorbent bed may require more frequent changing, but in general it should last for several months. The adsorbent-filter module is as easy to change as the battery pack. The adsorbent bed—filter pack is preferably stored and/or sold housed in a moisture impenetrable pouch or container.

Battery Pack for Portable Oxygen Concentrator

Conventional portable oxygen concentrators deal with additional run-time by various methods. For example, the AirSep "Freestyle" unit offers a battery belt ("AirBelt") for additional run-time beyond the internal battery pack. But the belt is worn by the user and attached to the device through a power cord. Respironics ("EverGo") has two battery compartments allowing the user to double their available run-time by inserting one additional battery pack. The battery weight goes up by increments of 1 battery pack (each approximately 1.5 lbs).

U.S. Pat. No. 7,510,601 discloses the use one or more batteries mounted externally on the portable oxygen concentrator. It is common practice for other portable battery operated devices (e.g. cordless drills, saws, etc.) to mount the battery pack externally to the device. For example, U.S. Pat. Nos. 3,952,239 and 6,515,451 describe various battery operated tools with interchangeable battery packs. A more flexible approach to battery utilization is used in the various embodiments of the present invention.

A problem with portable oxygen concentrators is the balance between battery weight and available run-time of the unit. This approach is to allow for a flexible battery pack with minimum impact on the size/weight and available space utilized by the ultra rapid cycle portable oxygen concentrator.

In certain embodiments, the battery pack for the ultra rapid cycle portable oxygen concentrator are incorporated as part of device, yet removable, and take up less volume, than a device that has a housing that the battery pack is inserted into. In many embodiments, the general overall volume is less, since no battery compartment is required. Also, since the pack may be mounted outside on the case, the different battery packs may have the same general shape, conforming to the overall device design, but can have different mass or weights that allow for different quantities of battery cells. Without having the constraint of the housing within the device, the battery pack can conform to the overall shape and design of the device, rather than the battery pack appearing to be a separate component mounted to the device.

Allowing for different battery packs gives the user a flexibility of choosing how much run-time vs. weight carried. If the user is going to operate the unit for an extended period when there might be unknown access to battery charging, the user could opt for the longer run-time, yet heavier battery pack. The lighter pack could be chosen for quick trips or where weight might be more of an issue (such as while exercising). Illustrated below, this embodiment would allow for weight increments of 0.5 pounds or the weight of a grouping of battery cells sufficient to supply the desired voltage.

Figure 6A:
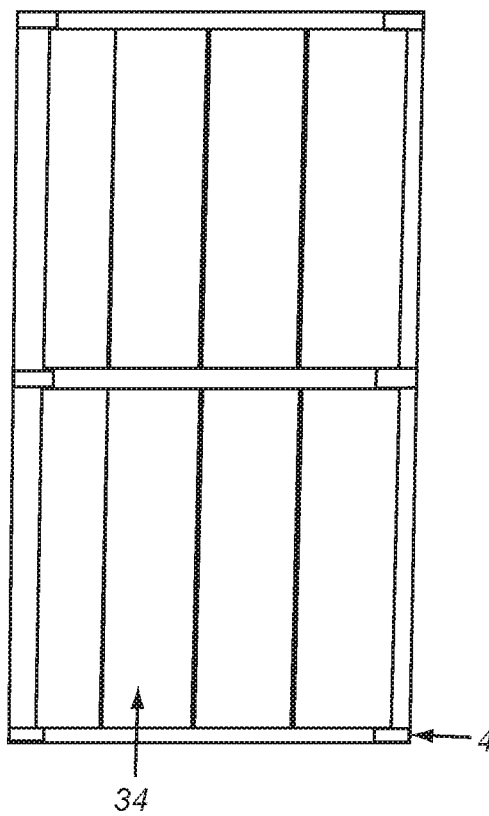
FIGS. 6A, 6B, and 6C are back, top and bottom views, respectively, of the battery pack configured with fifteen cells (eight on top layer, seven on bottom layer).
Figure 6B:
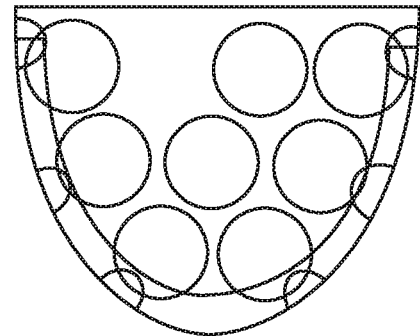
Figure 6C:
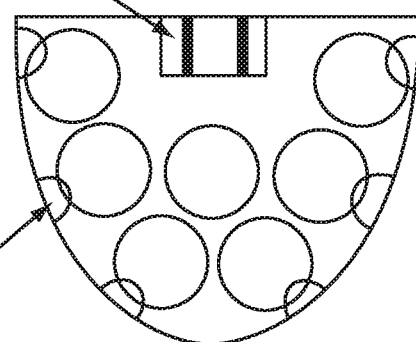

FIGS. 6A, 6B, and 6C are back, top and bottom views, respectively, of the battery pack configured with 15 cells (8 on top layer, 7 on bottom layer).

Figure 7:
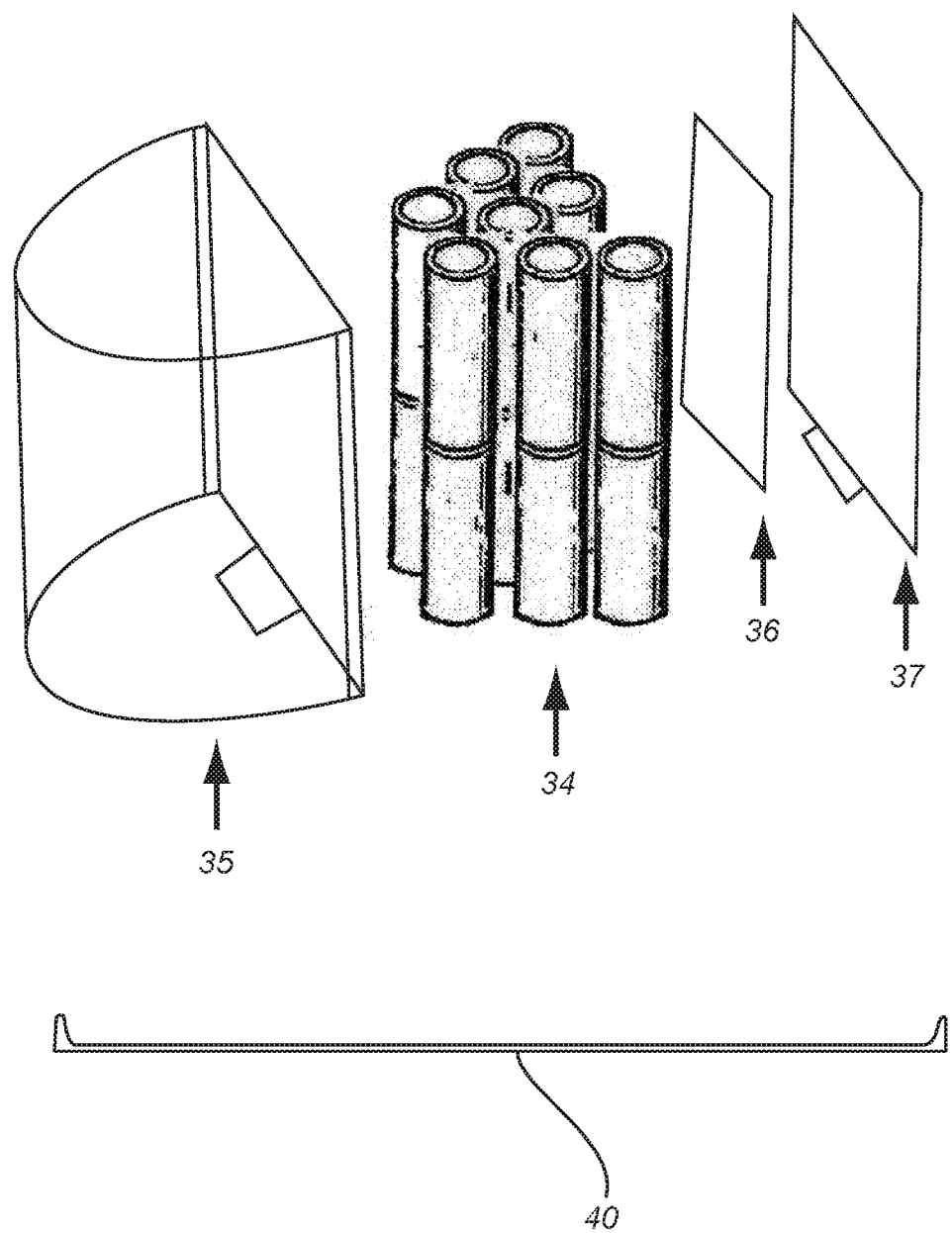
FIG. 7 is an exploded perspective view of the fifteen cell battery pack with the battery cells, PCM unit, and back of the battery case.

FIG. 7 is an exploded perspective view of the 15 cell battery pack 40 with the battery cells 34, protection circuit module (PCM) unit 36, and back plate 37 of the battery pack case 35.

FIGS. 6 and 7 illustrate an embodiment of the battery pack according to the principles of the current invention. The battery pack case 35 may be shaped to conform to the overall exterior style of the device, and may not be housed within the device, but mounted to appear as part of the device. This embodiment shown in FIGS. 6 and 7 utilizes a curved shape that mimics the overall design of the portable oxygen concentrator. The inclusion of the battery pack 40 on the device completes the shape and design of the portable oxygen concentrator 43. Battery cells 24 are arranged within the case 35 to conform to the general curved shape of the case, filling the available area, and secured to the case through tabs 41 above and below the battery cells 34. Space unfilled by batteries (or wiring, connectors or the PCM) can be left open, or filled with foam.

Recessed female connectors for the positive and negative terminals 42 may be on the battery pack 40 illustrated in FIG. 6C, the connectors may be blade style or other quick release connector type.

FIG. 7 shows the arrangement of the battery pack case 35, battery cells 34, a protection circuit module (PCM) 36 is incorporated within the battery pack for over and under charge protection, and the back plate 37, which is where the guide rail can mate with a corresponding channel on the device case.

FIG. 8 is a side view of a portable oxygen concentrator system having a battery pack module 40 and the remainder of the portable oxygen concentrator module 43 where the battery pack handle 38 conforms to the portable oxygen concentrator's handle 39 to make it appear as a contiguous piece. The portable oxygen concentrator module 43 has a first partial handle portion 39. The battery pack module 40 has a second partial handle portion 38. The battery pack module 40 releasably connects to the portable oxygen concentrator module 43. The first partial handle portion of the portable oxygen concentrator module 43 and the second partial handle portion align to form a single integrated handle. The second partial handle portion 38 may be used to attach and remove the battery pack to and from the device.

The battery pack may be fastened to the remainder of the portable oxygen concentrator portion device through a quick release latch and have a guide rail on the mating surface side which aids in aligning the pack while it is mounted onto the portable device (not shown in FIG. 8).

In certain embodiments, the battery pack 40 has the same height, but allows for variation in overall volume, width and depth, and has different quantities of secondary battery cells wired to deliver the same voltage. The varying quantity of battery cells gives the flexibility of more power and run-time (but heavier weight), or less run-time (but lighter weight), while still conforming to the overall shape of the battery pack 40. FIG. 7 illustrates the design that allows for two rows high of battery cells.

In certain embodiments, the battery cells may be grouped and wired in series and the groups arranged and wired in parallel to deliver the necessary voltage and power. For example, an 18.5 V battery pack using rechargeable lithium ion battery cells (2600 mAhr 18650 cells) would have five 3.7 V cells wired in series to give 18.5V, 2 or more of these groups wired in parallel together give additional power. The group of five cells has the maximum capacity of 2.6 Amp-hours, wiring additional groups in parallel increases the available power. Two groups would yield 5.2 A-hrs, 3 groups would supply 7.8 A-hrs. A 5 cell series-set weighs approximately 0.5 pounds, two groups would weigh approximately 1 pound, and longer run-time packs would increase in increments of approximately 0.5 pound.

In certain embodiments, the battery cells may be grouped in a series of 3, 4, 5 or more cells to yield the desired voltage. Groups of these cells may be wired together (and to the PCM) in groups of one or more to yield the desired power capacity.

Selection criteria of the battery cells includes lightweight with high energy density, including but not limited to: lithium ion, lithium-polymer, silver-zinc, or other rechargeable battery cells.

Oxygen Sensor for Portable Oxygen Concentrator

Oxygen concentrators typically include a sensor for measuring oxygen purity and a way to alert the patient should purity dip below 85%. Portable oxygen concentrators typically use an electrochemical sensor (also galvanic cell, and micro-fuel cell type sensors). Such sensors provide an electrical voltage signal linear to oxygen purity. The voltage results from a chemical reaction between sensor materials and oxygen passing into the sensor. Somewhat like a battery, over time the signal changes as sensor electrolytes are consumed. This reaction accelerates in high (85%+) oxygen conditions present in portable oxygen concentrators.

Electrochemical advantage/disadvantage. This sensor requires very low power (less than 0.1 watt), needed only for an auxiliary circuit providing signal analysis (comparison with minimum acceptable oxygen level) and LED status display. The signal is linear to oxygen purity. Sensor warm-up is not required. However, the sensor has a short lifetime (a few months to a year from date of manufacture, even when stored), especially in high purity oxygen environment, requires periodic recalibration, and may require periodic replacement. The accuracy is about 2% to 5%.

Home stationary oxygen concentrators have fewer limitations on power consumption and therefore may use a long lifetime zirconium based oxygen sensor. Such sensor technology is a spin-off from the automobile industry. This sensor requires more power due to a heater and operation at 450° C. The output current is non-linear to oxygen purity. For example, the Fujikura FCX-UWC zirconium based sensor is designed for continuous 75% to 95% oxygen purity, output is 8 to 20 micro-amp, with the heater consuming 1.5 watt.

Zirconium advantage/disadvantage. This sensor has a long lifetime (10,000 hours, actual operation), never needs recalibration, and never requires replacement. Accuracy is 1%. However, it requires large power (1.5+ watt), and a long (4.5 minute) warm-up time followed by a (0.5 minute) settling time.

In view of the advantages and disadvantages noted above, a need has arisen for a long lifetime oxygen sensor suitable for portable oxygen concentrators. The zirconium based sensor is a good candidate if only the power consumption could be reduced.

In one embodiment, the zirconium-based oxygen sensor is operated with less power, which permits the sensor to be used in a portable oxygen concentrator of the invention. The method involves intermittent operation and pulse-width modulation of the sensor's heater control. Using these new methods, the average power is reduced to about 10% to about 20% of normal.

Figure 9:
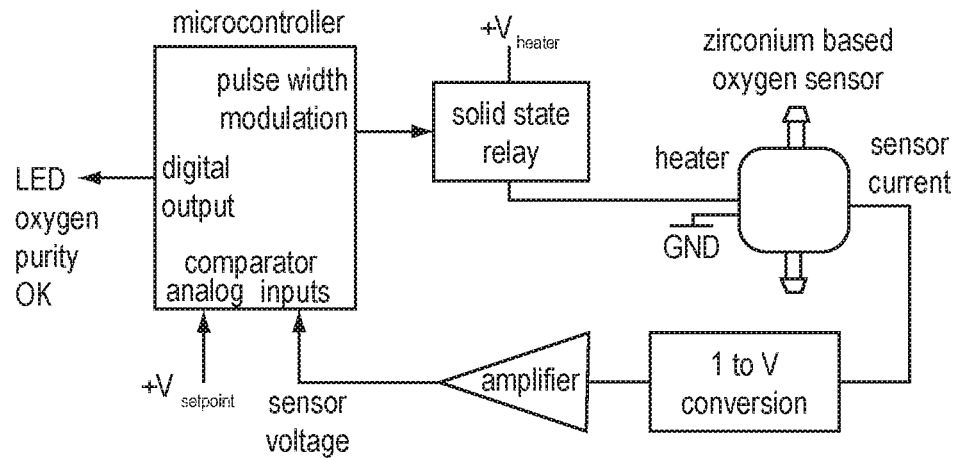
FIG. 9 is a block diagram of an oxygen sensor electronics.
Figure 10:
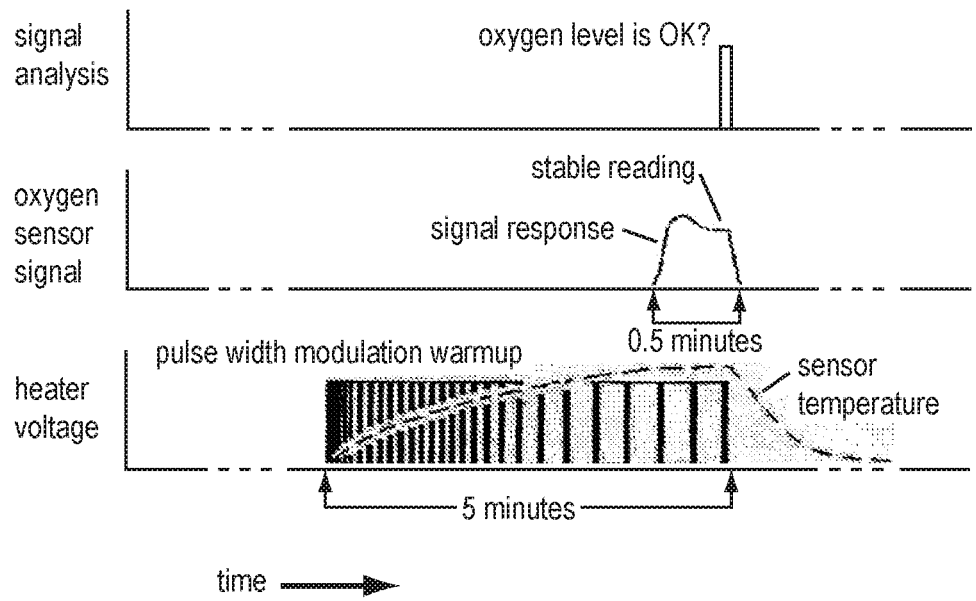
FIG. 10 is an illustration of the oxygen sensor signal timing.

The zirconium based oxygen sensor electronic controls are shown in FIG. 9 and timing is shown in FIG. 10. The oxygen sensor conserves power by being turned off when an oxygen reading is not required. Typically, the microcontroller orchestrates a reading at 10 minutes after startup of the concentrator, and after another 30 minutes. Thereafter readings may be taken as infrequently as once each hour.

Each oxygen reading involves several steps carried out over a 5 minute period. This begins with a 4.5 minute warm-up to 450° C., followed by sufficient time for the signal to settle, followed by capture of the reading, and analysis. Heating of the sensor is handled by the microcontroller via a periodically applied pulse width modulation (PWM) signal to the solid state relay. The PWM is varied by frequency and/or duty cycle. The sensor's current output is converted to a voltage signal, amplified, and then input by the microcontroller's comparator. That reading is compared to a voltage set-point representing 85% oxygen purity. When the sensor reading is above set-point then the LED for oxygen purity ok is lighted. In case the oxygen level dips below 85%, the microcontroller firmware alerts the patient by flashing the LED and/or sounding an alarm. In the extreme case of persistent low oxygen levels, the microcontroller can initiate complete shutdown of the concentrator.

The above described method translates to an average power consumption of 0.2 watts for the zirconium based oxygen sensor compared with 2 watts for continuous operation. This value assumes 5 minutes operation each hour (that is, 5 min/60 min×2 watt=0.2 watt on average). This is an acceptable power level for the oxygen sensor, because the rest of the concentrator, depending upon oxygen setting, requires about 20 watts to about 50 watts.

Optional Features of Portable Oxygen Concentrator

The device may also comprise:
a source of a fluid mixture comprising at least a first component and a second component;
a collector of said first component;
a collector of an exhaust fluid stream enriched in said second component and depleted in said first component;
an fluid induction unit.
a data collection component;
a user interface component; and/or
a vacuum unit.

The sorption device may further comprise valves, including mechanical check valves, Tesla valves, and pneumatic diode valves, although additional valves are not preferred.

Docking Station

In an alternate embodiment, the portable oxygen concentrator may be part of a system where the portable oxygen concentrator may be removed by the user (for example, when a stationary unit is available or when supplemental oxygen is not needed) and placed in a docking station with a battery recharge to recharge the battery cell(s).

The methods, devices, and systems of the invention may be microprocessor controlled. The adsorption devices of the invention may comprise at least one power conditioning device. Suitable power conditioning devices include a voltage changing device (such as a piezoelectric transformer or a high frequency transformer), a poly-phase frequency generator, a poly-phase frequency amplifier (a power transistor, a complimentary metal oxide semiconductor (CMOS), an insulated gate bipolar transistor (IGBT)), or a combination thereof.

Since the devices and systems of the invention are used for concentrating oxygen for medical use, the devices and systems may preferably be small enough in size and weight to be easily carried by an elderly person or an individual with compromised health. The devices or systems may be supported by a purse-like or "fanny pack"-type holder with a shoulder strap.

When used for supplying medical oxygen, the device may further comprise a muffler to dampen noise, an optional cannula, and/or an optional conserver. The cannula may be held by, contained in, or hidden by the shoulder strap described above. The conserver that may be used preferably senses inspiration and either opens a valve admitting oxygen to the cannula, or the sensor controls the cycle time of the portable oxygen concentrator.

It will be apparent to those skilled in the art that various modifications and variations can be made in the present invention and specific examples provided herein without departing from the spirit or scope of the invention. Thus, it is intended that the present invention cover the modifications and variations of this invention that come within the scope of any claims and their equivalents.

EXAMPLES

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

Example 1

Figure 13:
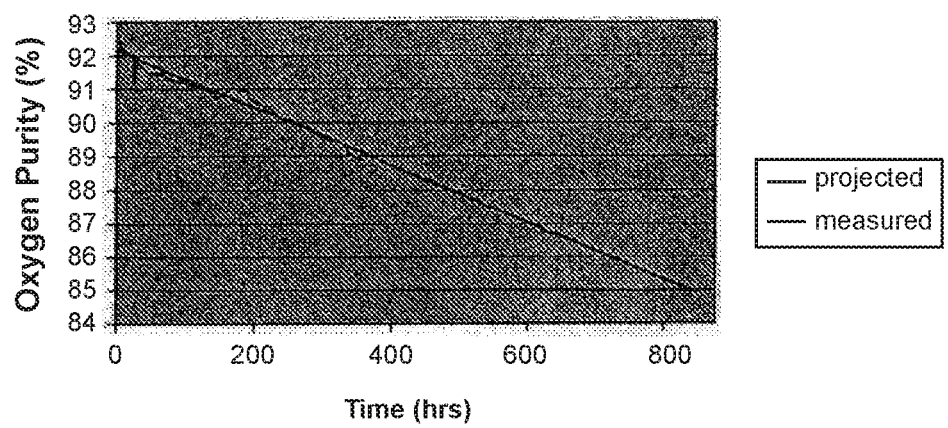
FIG. 13 is a plot of % oxygen purity as a function of time in hours to show the drop in oxygen purity (input air had a relative humidity of 75%).

Performance of regenerated adsorbent output of oxygen at high levels of relative humidity (at 75% relative humidity)

was measured. The data is shown in FIG. 13. As can be seen in FIG. 13, at 75% relative humidity for input air, oxygen production remains above an 88% purity level for a period of 22 days of continual operation (equivalent to approximately 65 patient operation days). No moisture removal technology was incorporated into the testing regime in order to obtain a baseline of adsorbent performance.

Example 2: Cycle Time Selection for Adsorbent Bed

Figure 14:
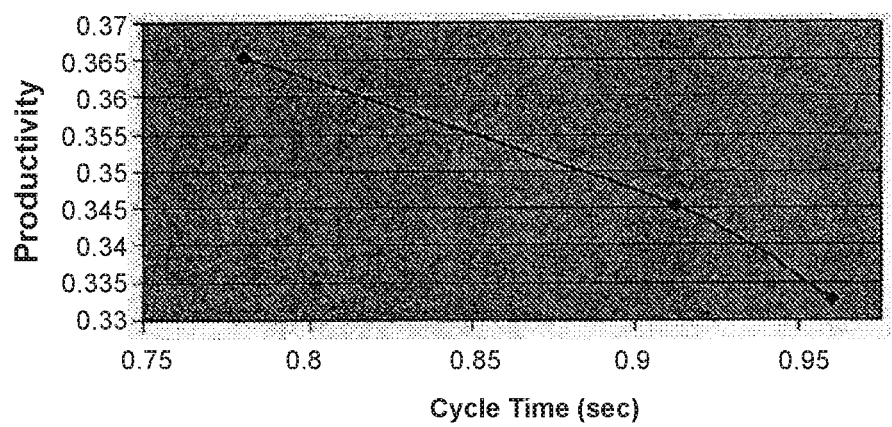
FIG. 14 is a plot of productivity as a function of cycle time in seconds for a 0.7 inch ID×3 inch long absorbent bed (contactor).

Tests were conducted using an 18 mm diameter, 76 mm long adsorbent bed that holds approximately 12 grams of the advanced adsorbent. The goal of these tests was to determine the cycle time that leads to the highest possible efficiency. In order to do this, the flow rate of air into the bed and the flow rate of the oxygen-enriched product out of the bed were measured, in order to calculate the productivity (also known as recovery rate) of the bed. Productivity is calculated as follows:

$$P = \frac{Q_{oxygen} \times O_2 \text{Purity}}{Q_{air} \times 0.209}$$

Where P is productivity, $Q_{oxygen}$ is the flow rate of oxygen, $O_2$ Purity is the decimal purity of Oxygen, and $Q_{air}$ is the flow rate of air, which is multiplied by 0.209 (the nominal oxygen purity of atmospheric air) to obtain the amount of oxygen in the air that passed through the bed. In this case, a cycle of 0.78 seconds duration produces 0.8 LPM of high purity (95% for the duration of the test) oxygen, while requiring approximately 10 LPM of air input. This meets the requirements set out for the portable medical oxygen concentrator of the invention. The results are shown in FIG. 14.

Example 3: Adsorbent Bed Dimensions (Length/Diameter Ratio) and Quantity of Adsorbent Several different sizes of adsorbent bed were tested to determine the proper dimensions for a bed to be used with the advanced adsorbent.

| Length (mm) | Diameter (mm) | L/D ratio | Mass Ads (g) | Max Output (LPM) |
|---|---|---|---|---|
| 76 | 16 | 4.75 | 9.2 | 0.6# |
| 101 | 16 | 6.31 | 12.2 | 0.74* |
| 114 | 16 | 7.125 | 13.8 | 0.8* |
| 76 | 18 | 4.22 | 11.6 | 0.8^ |

*= requires a pressure input of 270 kPa absolute
^= requires a pressure input of 225 kPa absolute
= requires a pressure input of 250 kPa absolute From the results of the tests, it can be shown that an L/D ratio of 4.22 worked the best in terms of energy efficiency because it requires less pressure to produce adequate output.

Figure 15:
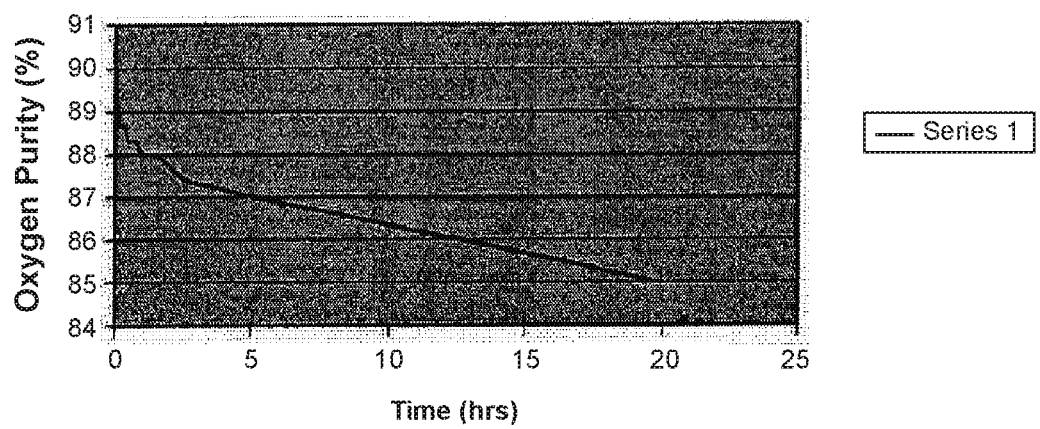
FIG. 15 is a plot of % oxygen purity as a function of time in hours to show the drop in oxygen purity using adsorbent beds that hold about 0.95 g of adsorbent.
Figure 16:
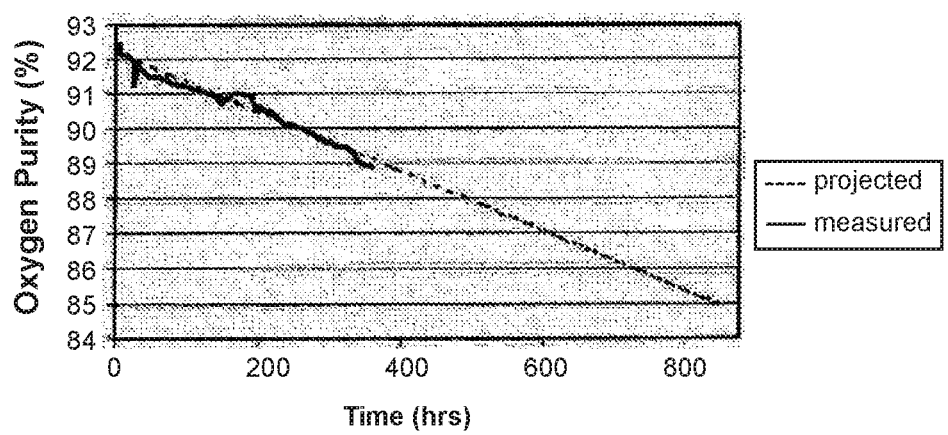
FIG. 16 is a plot of % oxygen purity (projected and measured) as a function of time in hours to show the drop in oxygen purity using adsorbent beds that hold about 10 g of adsorbent.

An additional consideration that affects the size of the adsorbent bed is the amount of time it is able to operate until it must be replaced because the performance has degraded due to water adsorption. It is possible to use 4 adsorbent beds that hold less than one gram of adsorbent, cycle them at 3-4 cycles per second, and produce the targeted output of 0.75 LPM of 85%+ oxygen, but they last for less than one day before they must either be replaced or regenerated by heating them and passing a dry purge gas through them to carry away the water that is liberated. FIGS. 15 and 16 show the degradation curves (at 60% relative humidity) for one adsorbent bed that holds less than one gram of adsorbent (FIG. 15), and for one adsorbent bed that holds approximately 10 grams of adsorbent (FIG. 16).

Example 4: Maximum Cycle Rates

Figure 17:
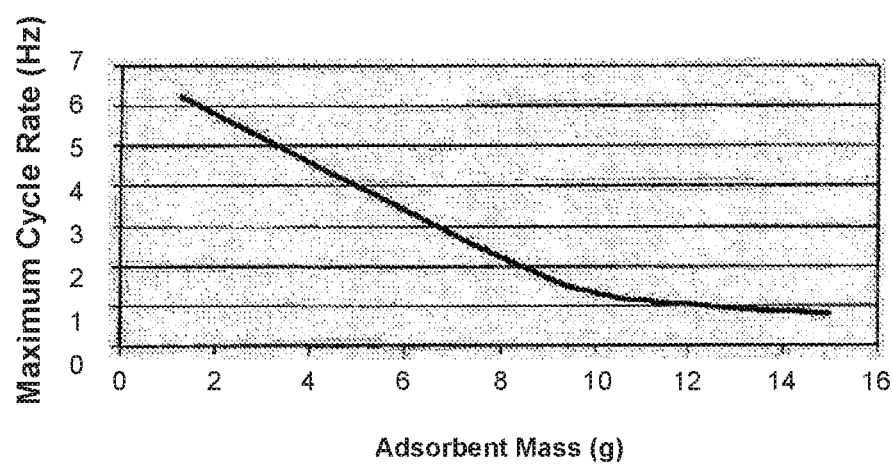
FIG. 17 is a plot showing the maximum cycle rate (in Hz) as a function of adsorbent mass (in grams) achieving at least 85% oxygen purity.

The maximum possible cycles rates while still achieving at least 85% purity of oxygen were determined using the advanced adsorbents employed in the invention. The results are shown in FIG. 17. A plot showing the maximum cycle rate (in Hz) as a function of adsorbent mass (in grams) achieveing at least 85% oxygen purity is presented in FIG. 17.

Example 5: Gas Flow

Function of the moisture permeable membrane is enhanced by two features of operation: a pressure and moisture differential across the material. To demonstrate the transfer of moisture from a moist air stream to a dry oxygen flow under these conditions, tests were performed. Using a container prepared with non-optimized adsorbent walls, moist air with relative humidity (RH) of 60% was introduced into the outer container as ultra-dry oxygen (RH=<0.1%) was concurrently flowed through the inner chamber. A pressure differential of 10 psi was maintained throughout the experiment along with a ten-fold decrease in flow between the moist and dry gas streams. After equilibrium was achieved, RH of the moist air decreased by 32% while the moisture level of the dry oxygen increased to 7%. The purity level of oxygen was unaltered during the experiment thereby confirming the impervious nature of the adsorbent material to gases.

When ranges are used herein for physical properties, such as molecular weight, or chemical properties, such as chemical formulae, all combinations, and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A portable oxygen concentrator, comprising:
    a passageway for compressed fresh air;
    a conserver;
    an exhaust port; and
    at least one moisture control unit comprising a barrier material positioned between said passageway and said conserver, between said passageway and said exhaust port, or between said passageway and both said conserver and said exhaust port, wherein said moisture control unit functions to remove moisture from compressed air, to provide moisture to dry product gas, and to sequester moisture upon shutdown.

2. The portable oxygen concentrator of claim 1, wherein said barrier material comprises an adsorbent; and wherein said adsorbent is not gas permeable.

3. The portable oxygen concentrator of claim 2, wherein said barrier material comprises alumina.

4. The portable oxygen concentrator of claim 1, wherein said moisture control unit functions to reject heat from compressed air.

5. A portable oxygen concentrator, comprising:
- a passageway for compressed fresh air;
- a conserver;
- an exhaust port; and
- at least one moisture control unit comprising a barrier material positioned between said passageway and said conserver, between said passageway and said exhaust port, or between said passageway and both said conserver and said exhaust port, wherein said at least one moisture control unit further comprises at least one co-axial container comprising an outer chamber and an inner chamber, wherein said inner chamber is formed from a water-permeable material, wherein said water-permeable material is not permeable to gases, wherein said water-permeable material comprises a hydroscopic adsorbent material and an optional binder.

6. The portable oxygen concentrator of claim 5, wherein said outer chamber is formed from a lightweight metal.

7. The portable oxygen concentrator of claim 5, wherein said outer chamber is formed from aluminum.

8. The portable oxygen concentrator of claim 5, wherein said hydroscopic adsorbent material is an alumina, an aluminum oxide, a silica gel, or a combination thereof.

9. A portable oxygen concentrator, comprising:
- a passageway for compressed fresh air;
- a conserver;
- an exhaust port; and
- at least one moisture control unit comprising a barrier material positioned between said passageway and said conserver, between said passageway and said exhaust port, or between said passageway and both said conserver and said exhaust port, wherein said moisture control unit functions to reject heat from at least one of a reservoir of compressed air and a reservoir of product gas.

* * * * *